(12) United States Patent
Dintenfass

(10) Patent No.: US 10,034,608 B1
(45) Date of Patent: Jul. 31, 2018

(54) SYSTEM FOR RECEIVING TRANSMISSIONS FROM DISPARATE NODE AND TRIGGERING AUTOMATIC PORTAL ACTION

(71) Applicant: Bank of America Corporation, Charlotte, NC (US)

(72) Inventor: Katherine Dintenfass, Lincoln, RI (US)

(73) Assignee: Bank of America Corporation, Charlotte, NC (US)

( * ) Notice: Subject to any disclaimer, the term of this patent is extended or adjusted under 35 U.S.C. 154(b) by 0 days.

(21) Appl. No.: 15/676,531

(22) Filed: Aug. 14, 2017

(51) Int. Cl.
G08B 21/00 (2006.01)
A61B 5/00 (2006.01)
G08B 21/04 (2006.01)
G06F 19/00 (2018.01)

(52) U.S. Cl.
CPC ............... *A61B 5/00* (2013.01); *G06F 19/00* (2013.01); *G08B 21/0453* (2013.01)

(58) Field of Classification Search
CPC ....... A61B 5/00; A61B 5/0002; A61B 5/0004; A61B 2/0015; A61B 5/002; A61B 5/0022; A61B 5/0024; G08B 21/00; G08B 21/0453; G08B 21/0461; G06F 19/00; G06F 19/34; G06F 19/3418
See application file for complete search history.

(56) References Cited

U.S. PATENT DOCUMENTS

| 4,481,583 A | 11/1984 | Mueller et al. |
| 4,890,227 A | 12/1989 | Watanabe et al. |
| 5,630,067 A | 5/1997 | Kindell et al. |
| 5,974,389 A | 10/1999 | Clark et al. |
| 6,086,216 A | 7/2000 | Huberman et al. |
| 6,233,623 B1 | 5/2001 | Jeffords et al. |
| 6,742,099 B1 | 5/2004 | Mendoza |
| 6,983,463 B1 | 1/2006 | Hunt |
| 7,174,379 B2 | 2/2007 | Agarwal et al. |
| 7,301,451 B2 * | 11/2007 | Hastings ................ A61B 5/411 128/903 |
| 7,302,450 B2 | 11/2007 | Benedetti et al. |
| 7,500,001 B2 | 3/2009 | Tameshige et al. |

(Continued)

FOREIGN PATENT DOCUMENTS

| CA | 2628396 A1 | 10/2009 |
| WO | 99/17194 A1 | 4/1999 |

*Primary Examiner* — Van Trieu

(74) *Attorney, Agent, or Firm* — Michael A. Springs; Moore & Van Allen PLLC; Patrick B. Horne

(57) ABSTRACT

A system for monitoring device data is provided. The system is configured to monitor, continuously, a computing device associated with the first user for an indication of a status change for a status of the first user; identify, from the computing device associated with the first user, the indication of the status change for the first user, where the indication of the status change was received from the first user via first user input to the computing device; identify a responsive action associated with the status change of the first user; and transmit a responsive action to a mobile computing device of a second user of the one or more users, wherein the responsive action alert activates the responder application to cause the mobile computing device of the second user to display a notification of the status change and the responsive action in real time.

20 Claims, 9 Drawing Sheets

(56) References Cited

U.S. PATENT DOCUMENTS

| | | |
|---|---|---|
| 7,640,210 B2 | 12/2009 | Bennett et al. |
| 7,702,644 B2 | 4/2010 | Bush et al. |
| 7,774,221 B2 | 8/2010 | Miller et al. |
| 7,890,354 B2 | 2/2011 | Trani |
| 7,945,458 B1 | 5/2011 | Jackson |
| 8,019,622 B2 | 9/2011 | Kaboff et al. |
| 8,046,249 B2 | 10/2011 | Hitz |
| 8,260,804 B2 | 9/2012 | Bush et al. |
| 8,682,952 B2 | 3/2014 | Kutzik et al. |
| 8,842,001 B2 * | 9/2014 | Gilham .................. A61B 5/746 340/539.1 |
| 9,384,652 B2 * | 7/2016 | Gilham .................. A61B 5/746 |
| 9,854,972 B2 * | 1/2018 | Mensinger ........... A61B 5/0002 |
| 2001/0042139 A1 | 11/2001 | Jeffords et al. |
| 2003/0074387 A1 | 4/2003 | Tanaka |
| 2006/0031509 A1 | 2/2006 | Ballette |
| 2007/0011683 A1 | 1/2007 | Helander |
| 2008/0077932 A1 | 3/2008 | Ruppach et al. |
| 2008/0126547 A1 | 5/2008 | Waldspurger |
| 2009/0199198 A1 | 8/2009 | Horii et al. |
| 2010/0011365 A1 | 1/2010 | Gerovac et al. |
| 2010/0306163 A1 | 12/2010 | Beaty et al. |
| 2011/0276977 A1 | 11/2011 | van Velzen et al. |
| 2013/0104140 A1 | 4/2013 | Meng et al. |
| 2013/0191140 A1 | 7/2013 | Fotheringham et al. |
| 2015/0178458 A1 | 6/2015 | Pellinat et al. |
| 2016/0027051 A1 | 1/2016 | Gross |
| 2016/0048934 A1 | 2/2016 | Gross |
| 2016/0232625 A1 | 8/2016 | Akutagawa |
| 2016/0371620 A1 | 12/2016 | Nascenzi et al. |
| 2017/0308767 A1 | 10/2017 | Kodimer |
| 2017/0352122 A1 | 12/2017 | Markarian |

\* cited by examiner

004

PROVIDE A RESPONDER APPLICATION TO ONE OR MORE USERS ASSOCIATED WITH A FIRST USER FOR INSTALLATION ON REMOTE COMPUTING DEVICES OF THE ONE OR MORE USERS
400

MONITOR, CONTINUOUSLY, A COMPUTING DEVICE ASSOCIATED WITH THE FIRST USER FOR AN INDICATION OF A STATUS CHANGE FOR A STATUS OF THE FIRST USER
401

IDENTIFY, FROM THE COMPUTING DEVICE ASSOCIATED WITH THE FIRST USER, THE INDICATION OF THE STATUS CHANGE FOR THE FIRST USER
402

IN RESPONSE TO IDENTIFYING THE INDICATION OF THE STATUS CHANGE FOR THE FIRST USER, IDENTIFY A RESPONSIVE ACTION ASSOCIATED WITH THE STATUS CHANGE OF THE FIRST USER
403

IN RESPONSE TO DETERMINING THE RESPONSIVE ACTION, TRANSMIT A RESPONSIVE ACTION ALERT OVER A WIRELESS COMMUNICATION CHANNEL TO A MOBILE COMPUTING DEVICE OF A SECOND USER OF THE ONE OR MORE USERS
404

FIGURE 4

007

RECEIVE, FROM A COMPUTING DEVICE OF A FIRST USER, A REQUEST TO ESTABLISH A COLLABORATION FOR ADDRESSING ONE OR MORE FUTURE ACTIONS BETWEEN A PLURALITY OF USERS ASSOCIATED WITH THE FIRST USER
700

TRANSMIT, TO THE COMPUTING DEVICES OF EACH OF THE PLURALITY OF USERS, A REQUEST TO CONTRIBUTE TO THE ONE OR MORE FUTURE ACTIONS
701

RECEIVE, FROM A COMPUTING DEVICE OF A SECOND USER, AN ACCEPTANCE FROM THE SECOND USER
702

RECEIVE, FROM A COMPUTING DEVICE OF A THIRD USER, AN ACCEPTANCE FROM THE THIRD USER
703

IDENTIFY A FIRST FUTURE ACTION OF THE ONE OR MORE FUTURE ACTIONS AND A TOTAL RESOURCE AMOUNT ASSOCIATED WITH ADDRESSING THE FIRST FUTURE ACTION
704

TRANSMIT, TO THE COMPUTING DEVICE OF THE SECOND USER, A REQUEST TO APPROVE A TRANSFER OF A FIRST AMOUNT OF RESOURCES FROM THE RESOURCE ACCOUNT OF THE SECOND USER TO A COMBINED RESOURCE ACCOUNT ASSOCIATED WITH ADDRESSING THE FIRST FUTURE ACTION
705

TRANSMIT, TO THE COMPUTING DEVICE OF THE THIRD USER, A REQUEST TO APPROVE A TRANSFER OF A SECOND AMOUNT OF RESOURCES FROM THE RESOURCE ACCOUNT OF THE THIRD USER TO A COMBINED RESOURCE ACCOUNT ASSOCIATED WITH ADDRESSING THE FIRST FUTURE ACTION
706

FIGURE 7A

007

RECEIVE, FROM THE COMPUTING DEVICE OF THE SECOND USER, AN ACCEPTANCE TO TRANSFER THE FIRST AMOUNT OF RESOURCES FROM THE RESOURCE ACCOUNT OF THE SECOND USER TO THE COMBINED RESOURCE ACCOUNT
707

TRANSFER THE FIRST AMOUNT OF RESOURCES FROM THE RESOURCE ACCOUNT OF THE SECOND USER TO THE COMBINED RESOURCE ACCOUNT
708

RECEIVE, FROM THE COMPUTING DEVICE OF THE THIRD USER, AN ACCEPTANCE TO TRANSFER THE SECOND AMOUNT OF RESOURCES FROM THE RESOURCE ACCOUNT OF THE THIRD USER TO THE COMBINED RESOURCE ACCOUNT
709

TRANSFER THE SECOND AMOUNT OF RESOURCES FROM THE RESOURCE ACCOUNT OF THE THIRD USER TO THE COMBINED RESOURCE ACCOUNT
710

TRANSFER THE TOTAL RESOURCE AMOUNT FROM THE COMBINED RESOURCE ACCOUNT TO ONE OR MORE MERCHANTS ASSOCIATED WITH THE FIRST FUTURE ACTION
711

FIGURE 7B

800 — PROVIDE A RESPONDER APPLICATION TO ONE OR MORE USERS ASSOCIATED WITH A FIRST USER FOR INSTALLATION ON REMOTE COMPUTING DEVICES OF THE ONE OR MORE USERS

801 — MONITOR, CONTINUOUSLY, A COMPUTING DEVICE ASSOCIATED WITH THE FIRST USER FOR AN INDICATION OF A STATUS CHANGE FOR A STATUS OF THE FIRST USER

802 — IDENTIFY, FROM THE COMPUTING DEVICE ASSOCIATED WITH THE FIRST USER, THE INDICATION OF THE STATUS CHANGE FOR THE FIRST USER, WHERE THE INDICATION OF THE STATUS CHANGE WAS RECEIVED FROM THE FIRST USER VIA INPUT TO THE COMPUTING DEVICE

803 — IN RESPONSE TO IDENTIFYING THE INDICATION OF THE STATUS CHANGE FOR THE FIRST USER, IDENTIFY A RESPONSIVE ACTION ASSOCIATED WITH THE STATUS CHANGE OF THE FIRST USER

804 — IN RESPONSE TO DETERMINING THE RESPONSIVE ACTION, TRANSMIT A RESPONSIVE ACTION ALERT OVER A WIRELESS COMMUNICATION CHANNEL TO A MOBILE COMPUTING DEVICE OF A SECOND USER OF THE ONE OR MORE USERS

SYSTEM FOR RECEIVING TRANSMISSIONS FROM DISPARATE NODE AND TRIGGERING AUTOMATIC PORTAL ACTION

FIELD OF THE INVENTION

The present invention embraces a system for monitoring device data.

BACKGROUND

With recent developments in Internet technology, users may use online tools to manage resources for a third party. Conventional methods may include using online websites to manually manage resources. That said, there are a number of technical problems with using conventional online systems in this manner. In particular, the processes and interfaces of current systems lead to inefficiencies of computing resources such as processing power, memory, and network bandwidth.

Accordingly, there is a need for a resource management system that allows users to manage resources for a third party in an efficient manner.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Embodiments of the present invention provide a system for distributed server data management. The system comprises a resource management server, which comprises a processor; a communication interface; and a memory having a database and a resource management server application stored therein. The resource management server application, when executed by the processor, causes the processor to receive, via a user device associated with a user, a request to manage a resource on behalf of a third party; recall historical data associated with the third party from the historical database; detect, via a data analytics engine, a potential future action of the user; and display, via a graphical interface, a recommended future action to the user.

In some embodiments, the resource management server application further causes the processor to receive, from the user, an approval of the recommended future action; open a communication channel with an external server, wherein the external server comprises data associated with the third party and the resource of the third party; and modify the data associated with the resource on behalf of the third party in accordance with the recommended future action.

In some embodiments, the resource management server application further causes the processor to receive, from the user, a request to authorize a second user to manage the resource; assign, to the second user, log-in credentials corresponding to a second user device associated with the second user; receive the log-in credentials from the second user device; and authorize the second user to manage the resource on behalf of the third party.

In some embodiments, the system allows the second user full access to the historical data associated with the third party.

In some embodiments, the system restricts the second user to limited access to the historical data associated with the third party.

In some embodiments, the user selects the degree to which the system restricts the second user.

Embodiments of the present invention also provide a computer program product for distributed server data management, comprising a non-transitory computer-readable storage medium having executable instructions for receiving, via a user device associated with a user, a request to manage a resource on behalf of a third party; recalling historical data associated with the third party from a historical database; detecting, via a data analytics engine, a potential future action of the user; and displaying, via a graphical interface, a recommended future action to the user.

In some embodiments, the computer program product further comprises executable instructions for receiving, from the user, an approval of the recommended future action; opening a communication channel with an external server, wherein the external server comprises data associated with the third party and the resource of the third party; and modifying the data associated with the resource on behalf of the third party in accordance with the recommended future action.

In some embodiments, the computer program product further comprises executable instructions for receiving, from the user, a request to authorize a second user to manage the resource; assigning, to the second user, log-in credentials corresponding to a second user device associated with the second user; receiving the log-in credentials from the second user device; and authorizing the second user to manage the resource on behalf of the third party.

In some embodiments, the computer program product further comprises executable instructions for allowing the second user full access to the historical data associated with the third party.

In some embodiments, the computer program product further comprises executable instructions for restricting the second user to limited access to the historical data associated with the third party.

In some embodiments, the user selects the degree to which the second user is restricted.

Embodiments of the present invention also provide a computer-implemented method of distributed server data management, the method comprising receiving, via a user device associated with a user, a request to manage a resource on behalf of a third party; recalling historical data associated with the third party from a historical database; detecting, via a data analytics engine, a potential future action of the user; and displaying, via a graphical interface, a recommended future action to the user.

In some embodiments, the method further comprises receiving, from the user, an approval of the recommended future action; opening a communication channel with an external server, wherein the external server comprises data associated with the third party and the resource of the third party; and modifying the data associated with the resource on behalf of the third party in accordance with the recommended future action.

In some embodiments, the method further comprises receiving, from the user, a request to authorize a second user to manage the resource; assigning, to the second user, log-in credentials corresponding to a second user device associated with the second user; receiving the log-in credentials from the second user device; and authorizing the second user to manage the resource on behalf of the third party.

In some embodiments, the method further comprises allowing the second user full access to the historical data associated with the third party.

In some embodiments, the method further comprises restricting the second user to limited access to the historical data associated with the third party.

In some embodiments, the user selects the degree to which the second user is restricted.

Embodiments of the present invention also provide a system for monitoring device data to cause remote mobile computing devices to alert users to take actions for updating a status of a different user. The system comprises a memory device; and one or more processing devices operatively coupled to the memory device. The one or more processing devices are configured to execute computer-readable program code to provide a responder application to one or more users associated with a first user for installation on remote computing devices of the one or more users; monitor, continuously, a computing device associated with the first user for an indication of a status change for a status of the first user; identify, from the computing device associated with the first user, the indication of the status change for the first user, wherein the indication of the status change was received from the first user via first user input to the computing device; in response to identifying the indication of the status change for the first user, identify a responsive action associated with the status change of the first user; and in response to determining the responsive action, transmit a responsive action alert over a wireless communication channel to a mobile computing device of a second user of the one or more users, wherein the responsive action alert activates the responder application stored on the mobile computing device of the second user to cause the mobile computing device of the second user to display a notification of the status change for the first user and the responsive action associated with the status change of the first user in real time.

In some embodiments, the one or more processing devices are further configured to execute computer-readable program code to in response to identifying the responsive action associated with the status change of the first user, compare the responsive action with a database comprising accepted responsibilities associated with each of the one or more users associated with the first user to determine a match between the responsive action and the second user.

In some embodiments, the one or more processing devices are further configured to execute computer-readable program code to in response to identifying the indication of the status change for the first user, identify an additional responsive action associated with the status change of the first user; and in response to determining the additional responsive action, transmit an additional responsive action alert over a wireless communication channel to a mobile computing device of a third user of the one or more users, wherein the additional responsive action alert activates the responder application stored on the mobile computing device of the third user to cause the mobile computing device of the third user to display the notification of the status change for the first user and the additional responsive action associated with the status change of the first user.

In some embodiments, the one or more processing devices are further configured to execute computer-readable program code to facilitate at least a portion of the responsive action.

In some embodiments, facilitating the at least the portion of the responsive action comprises initiating and processing a financial transaction associated with the responsive action.

In some embodiments, facilitating the at least the portion of the responsive action comprises displaying a current geographic location of the first user in real time on the mobile computing device of the second user.

In some embodiments, the computing device associated with the first user is configured to detect or measures a health indicator of the first user, a geographic location of the first user, or financial transactions of the first user for a triggering event associated with the status change; and in response to detecting the triggering event, transmit the indication of the status change.

Embodiments of the present invention also provide a computer program product for monitoring device data to cause remote mobile computing devices to alert users to take actions for updating a status of a different user, the computer program product comprising at least one non-transitory computer readable medium comprising computer readable instructions, the instructions comprising instructions for providing a responder application to one or more users associated with a first user for installation on remote computing devices of the one or more users; monitoring, continuously, a computing device associated with the first user for an indication of a status change for a status of the first user; identifying, from the computing device associated with the first user, the indication of the status change for the first user, wherein the indication of the status change was received from the first user via first user input to the computing device; in response to identifying the indication of the status change for the first user, identifying a responsive action associated with the status change of the first user; and in response to determining the responsive action, transmitting a responsive action alert over a wireless communication channel to a mobile computing device of a second user of the one or more users, wherein the responsive action alert activates the responder application stored on the mobile computing device of the second user to cause the mobile computing device of the second user to display a notification of the status change for the first user and the responsive action associated with the status change of the first user in real time.

In some embodiments, the computer readable instructions further comprise instructions for in response to identifying the responsive action associated with the status change of the first user, comparing the responsive action with a database comprising accepted responsibilities associated with each of the one or more users associated with the first user to determine a match between the responsive action and the second user.

In some embodiments, the computer readable instructions further comprise instructions for in response to identifying the indication of the status change for the first user, identifying an additional responsive action associated with the status change of the first user; and in response to determining the additional responsive action, transmitting an additional responsive action alert over a wireless communication channel to a mobile computing device of a third user of the one or more users, wherein the additional responsive action alert activates the responder application stored on the mobile computing device of the third user to cause the mobile computing device of the third user to display the notification of the status change for the first user and the additional responsive action associated with the status change of the first user.

In some embodiments, the computer readable instructions further comprise instructions for facilitating at least a portion of the responsive action.

In some embodiments, facilitating the at least the portion of the responsive action comprises initiating and processing a financial transaction associated with the responsive action.

In some embodiments, facilitating the at least the portion of the responsive action comprises displaying a current geographic location of the first user in real time on the mobile computing device of the second user.

In some embodiments, the computer readable instructions further comprise instructions for detecting or measures a health indicator of the first user, a geographic location of the first user, or financial transactions of the first user for a triggering event associated with the status change; and in response to detecting the triggering event, transmitting the indication of the status change.

Embodiments of the present invention also provide a computer implemented method for monitoring device data to cause remote mobile computing devices to alert users to take actions for updating a status of a different user, said computer implemented method comprising providing a computing system comprising a computer processing device and a non-transitory computer readable medium, where the computer readable medium comprises configured computer program instruction code, such that when said instruction code is operated by said computer processing device, said computer processing device performs the following operations: providing a responder application to one or more users associated with a first user for installation on remote computing devices of the one or more users; monitoring, continuously, a computing device associated with the first user for an indication of a status change for a status of the first user; identifying, from the computing device associated with the first user, the indication of the status change for the first user, wherein the indication of the status change was received from the first user via first user input to the computing device; in response to identifying the indication of the status change for the first user, identifying a responsive action associated with the status change of the first user; and in response to determining the responsive action, transmitting a responsive action alert over a wireless communication channel to a mobile computing device of a second user of the one or more users, wherein the responsive action alert activates the responder application stored on the mobile computing device of the second user to cause the mobile computing device of the second user to display a notification of the status change for the first user and the responsive action associated with the status change of the first user in real time.

In some embodiments, the method further comprises in response to identifying the responsive action associated with the status change of the first user, comparing the responsive action with a database comprising accepted responsibilities associated with each of the one or more users associated with the first user to determine a match between the responsive action and the second user.

In some embodiments, the method further comprises in response to identifying the indication of the status change for the first user, identifying an additional responsive action associated with the status change of the first user; and in response to determining the additional responsive action, transmitting an additional responsive action alert over a wireless communication channel to a mobile computing device of a third user of the one or more users, wherein the additional responsive action alert activates the responder application stored on the mobile computing device of the third user to cause the mobile computing device of the third user to display the notification of the status change for the first user and the additional responsive action associated with the status change of the first user.

In some embodiments, the method further comprises facilitating at least a portion of the responsive action.

In some embodiments, facilitating the at least the portion of the responsive action comprises (i) initiating and processing a financial transaction associated with the responsive action or (ii) displaying a current geographic location of the first user in real time on the mobile computing device of the second user.

In some embodiments, the method further comprises detecting or measures a health indicator of the first user, a geographic location of the first user, or financial transactions of the first user for a triggering event associated with the status change; and in response to detecting the triggering event, transmitting the indication of the status change.

Embodiments of the present invention also provide a system for configuring and executing a secure communication network for authorizing access to safeguarded resources, the system comprising a memory device; and one or more processing devices operatively coupled to the memory device, wherein the one or more processing devices are configured to execute computer-readable program code to receive a request from a first user to grant a second user access to an account associated with the first user; in response to receiving the request to grant the second user the access to the account associated with the first user, configure a secure dedicated communication channel between a computing device of the first user and a computing device of the second user; transmit, via the secure dedicated communication channel, to the computing device of the second user, the request to grant the second user the access to the account associated with the first user; receive, from the computing device of the second user, an acceptance of the request to grant the second user the access to the account associated with the first user; in response to receiving the acceptance, transmit control signals configured to cause the computing device of the second user to display an authentication challenge and a request for an input of an authentication challenge response; receive, from the computing device of the second user, the authentication challenge response; compare the received authentication challenge response with authentication data of the second user stored in a database to determine that the received authentication challenge response is acceptable; and in response to determining that the received authentication challenge response is acceptable, grant the second user with access rights to the account associated with the first user.

In some embodiments, the one or more processing devices are further configured to execute computer-readable program code to receive the request from the first user to grant the second user the access to the account associated with the first user, wherein the request to grant the second user the access to the account associated with the first user comprises an electronic authorization document associated with the access to the account associated with the first user; in response to determining that the received authentication challenge response is acceptable, transmit the electronic authorization document, via the secure dedicated communication channel, from the computing device of the first use to the computing device of the second user; receive, from the computing device of the second user, the electronic authorization document; determine that the electronic authorization document received from the computing device of the second user has successfully been completed; and in response to determining that the electronic authorization document has successfully been completed, grant the second user the access rights to the account associated with the first user.

In some embodiments, the one or more processing devices are further configured to execute computer-readable program code to receive the request from the first user to grant the second user the access to the account associated with the first user, wherein the request to grant the second user the access to the account associated with the first user is conditioned on an occurrence of a triggering event; receive an indication of the occurrence of the triggering event; and in response to receiving the indication of the occurrence of the triggering event, transmit, via the secure dedicated communication channel, to the computing device of the second user, the request to grant the second user the access to the account associated with the first user.

In some embodiments, the one or more processing devices are further configured to execute computer-readable program code to receive a request from the first user to grant a third user limited access to the account associated with the first user; in response to receiving the request to grant the third user the limited access to the account associated with the first user, configure a new secure dedicated communication channel between the computing device of the first user and a computing device of the third user; transmit, via the new secure dedicated communication channel, to the computing device of the third user, the request to grant the second user the limited access to the account associated with the first user; receive, from the computing device of the third user, an acceptance of the request to grant the third user the limited access to the account associated with the first user; in response to receiving the acceptance, transmit control signals configured to cause the computing device of the third user to display a limited authentication challenge and a request for an input of a limited authentication challenge response; receive, from the computing device of the third user, the limited authentication challenge response; compare the received limited authentication challenge response with authentication data of the third user stored in the database to determine that the received limited authentication challenge response is acceptable; and in response to determining that the received limited authentication challenge response is acceptable, grant the third user with limited access rights to the account associated with the first user.

In some embodiments, the one or more processing devices are further configured to execute computer-readable program code to terminate the access rights of the second user to the account associated with the first user after a predetermined period of time or in response to receiving a request from the first user to terminate the access rights of the second user.

In some embodiments, the request from the first user to grant the second user access to an account associated with the first user is associated with a request to grant the second user a power of attorney right with respect to at least the account associated with the first user.

In some embodiments, the request from the first user to grant the second user access to an account associated with the first user is associated with a request to grant the second user a legal right to perform an action on behalf of the first user that the second user would otherwise not have the legal right to perform.

Embodiments of the present invention also provide a computer program product for configuring and executing a secure communication network for authorizing access to safeguarded resources, the computer program product comprising at least one non-transitory computer readable medium comprising computer readable instructions, the instructions comprising instructions for receiving a request from a first user to grant a second user access to an account associated with the first user; in response to receiving the request to grant the second user the access to the account associated with the first user, configuring a secure dedicated communication channel between a computing device of the first user and a computing device of the second user; transmitting, via the secure dedicated communication channel, to the computing device of the second user, the request to grant the second user the access to the account associated with the first user; receiving, from the computing device of the second user, an acceptance of the request to grant the second user the access to the account associated with the first user; in response to receiving the acceptance, transmitting control signals configured to cause the computing device of the second user to display an authentication challenge and a request for an input of an authentication challenge response; receiving, from the computing device of the second user, the authentication challenge response; comparing the received authentication challenge response with authentication data of the second user stored in a database to determine that the received authentication challenge response is acceptable; and in response to determining that the received authentication challenge response is acceptable, granting the second user with access rights to the account associated with the first user.

In some embodiments, the computer readable instructions further comprise instructions for receiving the request from the first user to grant the second user the access to the account associated with the first user, wherein the request to grant the second user the access to the account associated with the first user comprises an electronic authorization document associated with the access to the account associated with the first user; in response to determining that the received authentication challenge response is acceptable, transmitting the electronic authorization document, via the secure dedicated communication channel, from the computing device of the first use to the computing device of the second user; receiving, from the computing device of the second user, the electronic authorization document; determining that the electronic authorization document received from the computing device of the second user has successfully been completed; and in response to determining that the electronic authorization document has successfully been completed, granting the second user the access rights to the account associated with the first user.

In some embodiments, the computer readable instructions further comprise instructions for receiving the request from the first user to grant the second user the access to the account associated with the first user, wherein the request to grant the second user the access to the account associated with the first user is conditioned on an occurrence of a triggering event; receiving an indication of the occurrence of the triggering event; and in response to receiving the indication of the occurrence of the triggering event, transmitting, via the secure dedicated communication channel, to the computing device of the second user, the request to grant the second user the access to the account associated with the first user.

In some embodiments, the computer readable instructions further comprise instructions for receiving a request from the first user to grant a third user limited access to the account associated with the first user; in response to receiving the request to grant the third user the limited access to the account associated with the first user, configuring a new secure dedicated communication channel between the computing device of the first user and a computing device of the third user; transmitting, via the new secure dedicated communication channel, to the computing device of the third user, the request to grant the second user the limited access to the account associated with the first user; receiving, from the computing device of the third user, an acceptance of the request to grant the third user the limited access to the account associated with the first user; in response to receiving the acceptance, transmitting control signals configured to cause the computing device of the third user to display a limited authentication challenge and a request for an input of a limited authentication challenge response; receiving, from the computing device of the third user, the limited authentication challenge response; comparing the received limited authentication challenge response with authentication data of the third user stored in the database to determine that the received limited authentication challenge response is acceptable; and in response to determining that the received limited authentication challenge response is acceptable, granting the third user with limited access rights to the account associated with the first user.

In some embodiments, the computer readable instructions further comprise instructions for terminating the access rights of the second user to the account associated with the first user after a predetermined period of time or in response to receiving a request from the first user to terminate the access rights of the second user.

In some embodiments, the request from the first user to grant the second user access to an account associated with the first user is associated with a request to grant the second user a power of attorney right with respect to at least the account associated with the first user.

In some embodiments, the request from the first user to grant the second user access to an account associated with the first user is associated with a request to grant the second user a legal right to perform an action on behalf of the first user that the second user would otherwise not have the legal right to perform.

Embodiments of the present invention also provide a computer implemented method for configuring and executing a secure communication network for authorizing access to safeguarded resources, said computer implemented method comprising providing a computing system comprising a computer processing device and a non-transitory computer readable medium, where the computer readable medium comprises configured computer program instruction code, such that when said instruction code is operated by said computer processing device, said computer processing device performs the following operations: receiving a request from a first user to grant a second user access to an account associated with the first user; in response to receiving the request to grant the second user the access to the account associated with the first user, configuring a secure dedicated communication channel between a computing device of the first user and a computing device of the second user; transmitting, via the secure dedicated communication channel, to the computing device of the second user, the request to grant the second user the access to the account associated with the first user; receiving, from the computing device of the second user, an acceptance of the request to grant the second user the access to the account associated with the first user; in response to receiving the acceptance, transmitting control signals configured to cause the computing device of the second user to display an authentication challenge and a request for an input of an authentication challenge response; receiving, from the computing device of the second user, the authentication challenge response; comparing the received authentication challenge response with authentication data of the second user stored in a database to determine that the received authentication challenge response is acceptable; and in response to determining that the received authentication challenge response is acceptable, granting the second user with access rights to the account associated with the first user.

In some embodiments, the method further comprises receiving the request from the first user to grant the second user the access to the account associated with the first user, wherein the request to grant the second user the access to the account associated with the first user comprises an electronic authorization document associated with the access to the account associated with the first user; in response to determining that the received authentication challenge response is acceptable, transmitting the electronic authorization document, via the secure dedicated communication channel, from the computing device of the first use to the computing device of the second user; receiving, from the computing device of the second user, the electronic authorization document; determining that the electronic authorization document received from the computing device of the second user has successfully been completed; and in response to determining that the electronic authorization document has successfully been completed, granting the second user the access rights to the account associated with the first user.

In some embodiments, the method further comprises receiving the request from the first user to grant the second user the access to the account associated with the first user, wherein the request to grant the second user the access to the account associated with the first user is conditioned on an occurrence of a triggering event; receiving an indication of the occurrence of the triggering event; and in response to receiving the indication of the occurrence of the triggering event, transmitting, via the secure dedicated communication channel, to the computing device of the second user, the request to grant the second user the access to the account associated with the first user.

In some embodiments, the method further comprises receiving a request from the first user to grant a third user limited access to the account associated with the first user; in response to receiving the request to grant the third user the limited access to the account associated with the first user, configuring a new secure dedicated communication channel between the computing device of the first user and a computing device of the third user; transmitting, via the new secure dedicated communication channel, to the computing device of the third user, the request to grant the second user the limited access to the account associated with the first user; receiving, from the computing device of the third user, an acceptance of the request to grant the third user the limited access to the account associated with the first user; in response to receiving the acceptance, transmitting control signals configured to cause the computing device of the third user to display a limited authentication challenge and a request for an input of a limited authentication challenge response; receiving, from the computing device of the third user, the limited authentication challenge response; comparing the received limited authentication challenge response with authentication data of the third user stored in the database to determine that the received limited authentication challenge response is acceptable; and in response to determining that the received limited authentication challenge response is acceptable, granting the third user with limited access rights to the account associated with the first user.

In some embodiments, the method further comprises terminating the access rights of the second user to the account associated with the first user after a predetermined period of time or in response to receiving a request from the first user to terminate the access rights of the second user.

In some embodiments, the request from the first user to grant the second user access to an account associated with the first user is associated with a request to grant the second user a power of attorney right with respect to at least the account associated with the first user.

Embodiments of the present invention also provide a system for extracting treatment information from a resource image, predicting a likely future event based on the extracted treatment information, and developing an action step to address the likely future event, the system comprising a memory device; and one or more processing devices operatively coupled to the memory device, wherein the one or more processing devices are configured to execute computer-readable program code to receive, from a computing device associated with a first user, an image of a resource; in response to receiving the image of the resource, extract treatment-related text from the image of the resource; identify, from the extracted treatment-related text, a treatment plan associated with the first user; analyze a treatment database comprising historical treatment plans of other users and significant events associated with the historical treatment plans to determine a likely future event for the first user, based on the identified treatment plan associated with the first user; identify, based on analyzing the treatment database, an expected date of the likely future event for the first user; identify, based on analyzing the treatment database, an expected cost of the likely future event for the first user; determine an action step for addressing the likely future event based on the expected date and the expected cost of the likely future event for the first user; and provide the action step to the computing device associated with the first user.

In some embodiments, the one or more processing devices are further configured to execute computer-readable program code to receive one or more additional images of one or more additional resources; extract additional treatment-related text from the one or more additional images of the one or more additional resources; and identify, from the extracted additional treatment-related text, the treatment plan associated with the first user.

In some embodiments, extracting the treatment-related text from the image of the resource comprises analyzing the image of the resource with an optical character recognition processes to extract the treatment-related text from the image of the resource and to populate one or more treatment template input fields with the extracted treatment-related text.

In some embodiments, the one or more processing devices are further configured to execute computer-readable program code to provide the action step to a computing device associated with a second user, wherein the second user is associated with the first user.

In some embodiments, the action step comprises an offer for a product configured to cover the expected cost of the likely future event.

In some embodiments, the one or more processing devices are further configured to execute computer-readable program code to provide a treatment application to the first user for installation on the computing device associated with the first user; receive a request to scan the resource from the computing device associated with the first user; and in response to receiving the request to scan the resource, transmit a scanning alert over a wireless communication channel to the computing device associated with the first user, wherein the scanning alert activates the treatment application stored on the computing device associated with the first user to cause a camera to capture the image of the resource.

In some embodiments, the treatment-related text includes at least one of a resource name, a resource dosage, a date of issuance of the resource, and a recommended or instructed frequency of use for the resource.

Embodiments of the present invention also provide a computer program product for extracting treatment information from a resource image, predicting a likely future event based on the extracted treatment information, and developing an action step to address the likely future event, the computer program product comprising at least one non-transitory computer readable medium comprising computer readable instructions, the instructions comprising instructions for receiving, from a computing device associated with a first user, an image of a resource; in response to receiving the image of the resource, extracting treatment-related text from the image of the resource; identifying, from the extracted treatment-related text, a treatment plan associated with the first user; analyzing a treatment database comprising historical treatment plans of other users and significant events associated with the historical treatment plans to determine a likely future event for the first user, based on the identified treatment plan associated with the first user; identifying, based on analyzing the treatment database, an expected date of the likely future event for the first user; identifying, based on analyzing the treatment database, an expected cost of the likely future event for the first user; determining an action step for addressing the likely future event based on the expected date and the expected cost of the likely future event for the first user; and providing the action step to the computing device associated with the first user.

In some embodiments, the computer readable instructions further comprise instructions for receiving one or more additional images of one or more additional resources; extracting additional treatment-related text from the one or more additional images of the one or more additional resources; and identifying, from the extracted additional treatment-related text, the treatment plan associated with the first user.

In some embodiments, extracting the treatment-related text from the image of the resource comprises analyzing the image of the resource with an optical character recognition processes to extract the treatment-related text from the image of the resource and to populate one or more treatment template input fields with the extracted treatment-related text.

In some embodiments, the computer readable instructions further comprise instructions for providing the action step to a computing device associated with a second user, wherein the second user is associated with the first user.

In some embodiments, the action step comprises an offer for a product configured to cover the expected cost of the likely future event.

In some embodiments, the computer readable instructions further comprise instructions for providing a treatment application to the first user for installation on the computing device associated with the first user; receiving a request to scan the resource from the computing device associated with the first user; and in response to receiving the request to scan the resource, transmitting a scanning alert over a wireless communication channel to the computing device associated with the first user, wherein the scanning alert activates the treatment application stored on the computing device associated with the first user to cause a camera to capture the image of the resource.

In some embodiments, the treatment-related text includes at least one of a resource name, a resource dosage, a date of issuance of the resource, and a recommended or instructed frequency of use for the resource.

Embodiments of the present invention also provide a computer implemented method for extracting treatment information from a resource image, predicting a likely future event based on the extracted treatment information, and developing an action step to address the likely future event, said computer implemented method comprising providing a computing system comprising a computer processing device and a non-transitory computer readable medium, where the computer readable medium comprises configured computer program instruction code, such that when said instruction code is operated by said computer processing device, said computer processing device performs the following operations: receiving, from a computing device associated with a first user, an image of a resource; in response to receiving the image of the resource, extracting treatment-related text from the image of the resource; identifying, from the extracted treatment-related text, a treatment plan associated with the first user; analyzing a treatment database comprising historical treatment plans of other users and significant events associated with the historical treatment plans to determine a likely future event for the first user, based on the identified treatment plan associated with the first user; identifying, based on analyzing the treatment database, an expected date of the likely future event for the first user; identifying, based on analyzing the treatment database, an expected cost of the likely future event for the first user; determining an action step for addressing the likely future event based on the expected date and the expected cost of the likely future event for the first user; and providing the action step to the computing device associated with the first user.

In some embodiments, the method further comprises receiving one or more additional images of one or more additional resources; extracting additional treatment-related text from the one or more additional images of the one or more additional resources; and identifying, from the extracted additional treatment-related text, the treatment plan associated with the first user.

In some embodiments, extracting the treatment-related text from the image of the resource comprises analyzing the image of the resource with an optical character recognition processes to extract the treatment-related text from the image of the resource and to populate one or more treatment template input fields with the extracted treatment-related text.

In some embodiments, the method further comprises providing the action step to a computing device associated with a second user, wherein the second user is associated with the first user.

In some embodiments, the action step comprises an offer for a product configured to cover the expected cost of the likely future event.

In some embodiments, the method further comprises providing a treatment application to the first user for installation on the computing device associated with the first user; receiving a request to scan the resource from the computing device associated with the first user; and in response to receiving the request to scan the resource, transmitting a scanning alert over a wireless communication channel to the computing device associated with the first user, wherein the scanning alert activates the treatment application stored on the computing device associated with the first user to cause a camera to capture the image of the resource.

Embodiments of the present invention also provide a system for linking and managing resources across multiple platforms for distribution to address future actions, the system comprising a memory device; and one or more processing devices operatively coupled to the memory device, wherein the one or more processing devices are configured to execute computer-readable program code to receive a request, from a computing device of a first user to establish a collaboration for addressing one or more future actions between a plurality of users associated with the first user; transmit a request, to computing devices of each of the plurality of users, to contribute to the one or more future actions; receive, from a computing device of a second user, an acceptance from the second user, wherein the acceptance from the second user is associated with an approval to link a resource account of the second user with the collaboration for addressing the one or more future actions; receive, from a computing device of a third user, an acceptance from the third user, wherein the acceptance from the third user is associated with an approval to link a resource account of the third user with the collaboration for addressing the one or more future actions; identify a first future action of the one or more future actions; identify a total resource amount associated with addressing the first future action; in response to identifying the total resource amount associated with addressing the first future action, transmit a request, to the computing device of the second user, to approve a transfer of a first amount of resources from the resource account of the second user to a combined resource account associated with addressing the first future action; in response to identifying the total resource amount associated with addressing the first future action, transmit a request, to the computing device of the third user, to approve a transfer of a second amount of resources from the resource account of the third user to the combined resource account associated with addressing the first future action; receive, from the computing device of the second user, an acceptance to transfer the first amount of resources from the resource account of the second user to the combined resource account; transfer the first amount of resources from the resource account of the second user to the combined resource account; receive, from the computing device of the third user, an acceptance to transfer the second amount of resources from the resource account of the third user to the combined resource account; transfer the second amount of resources from the resource account of the third user to the combined resource account; and transfer the total resource amount from the combined resource account to one or more merchants associated with the first future action.

In some embodiments, the one or more processing devices are further configured to execute computer-readable program code to receive, from a computing device of a fourth user, an acceptance from the fourth user, wherein the acceptance from the fourth user is associated with an approval to link a non-financial sub-action to be performed by the fourth user with the collaboration for addressing the one or more future actions; identify a need for the non-financial sub-action to be completed to address the first future action; and in response to identifying the need for the first non-financial sub-action to be completed, transmit a request to the computing device of the fourth user to perform the non-financial sub-action.

In some embodiments, the one or more processing devices are further configured to execute computer-readable program code to determine that the one or more future actions have been completed; and in response to determining that the one or more future actions have been completed, redistribute a remaining amount of resources from the combined resource account to the plurality of users.

In some embodiments, the remaining amount of resources is redistributed based on at least one of an agreement between the plurality of users, a proportional amount of resources provided by each of the plurality of users, and non-financial sub-actions provided by each of the plurality of users.

In some embodiments, the one or more processing devices are further configured to execute computer-readable program code to provide a line of resource credit associated with the combined resource account to the second user and the third user; and apply the line of resource credit to the combined resource account.

In some embodiments, the one or more processing devices are further configured to execute computer-readable program code to provide a savings product to the second user and the third user, wherein the savings product is configured to establish and grow a base set of resources set aside for addressing the one or more future actions.

In some embodiments, the first amount of resources and the second amount of resources are based on an agreement between the second user and the third user.

Embodiments of the present invention also provide a computer program product for linking and managing resources across multiple platforms for distribution to address future actions, the computer program product comprising at least one non-transitory computer readable medium comprising computer readable instructions, the instructions comprising instructions for receiving a request, from a computing device of a first user to establish a collaboration for addressing one or more future actions between a plurality of users associated with the first user; transmitting a request, to computing devices of each of the plurality of users, to contribute to the one or more future actions; receiving, from a computing device of a second user, an acceptance from the second user, wherein the acceptance from the second user is associated with an approval to link a resource account of the second user with the collaboration for addressing the one or more future actions; receiving, from a computing device of a third user, an acceptance from the third user, wherein the acceptance from the third user is associated with an approval to link a resource account of the third user with the collaboration for addressing the one or more future actions; identifying a first future action of the one or more future actions; identifying a total resource amount associated with addressing the first future action; in response to identifying the total resource amount associated with addressing the first future action, transmitting a request, to the computing device of the second user, to approve a transfer of a first amount of resources from the resource account of the second user to a combined resource account associated with addressing the first future action; in response to identifying the total resource amount associated with addressing the first future action, transmitting a request, to the computing device of the third user, to approve a transfer of a second amount of resources from the resource account of the third user to the combined resource account associated with addressing the first future action; receiving, from the computing device of the second user, an acceptance to transfer the first amount of resources from the resource account of the second user to the combined resource account; transferring the first amount of resources from the resource account of the second user to the combined resource account; receiving, from the computing device of the third user, an acceptance to transfer the second amount of resources from the resource account of the third user to the combined resource account; transferring the second amount of resources from the resource account of the third user to the combined resource account; and transferring the total resource amount from the combined resource account to one or more merchants associated with the first future action.

In some embodiments, the computer readable instructions further comprise instructions for receiving, from a computing device of a fourth user, an acceptance from the fourth user, wherein the acceptance from the fourth user is associated with an approval to link a non-financial sub-action to be performed by the fourth user with the collaboration for addressing the one or more future actions; identifying a need for the non-financial sub-action to be completed to address the first future action; and in response to identifying the need for the first non-financial sub-action to be completed, transmitting a request to the computing device of the fourth user to perform the non-financial sub-action.

In some embodiments, the computer readable instructions further comprise instructions for determining that the one or more future actions have been completed; and in response to determining that the one or more future actions have been completed, redistributing a remaining amount of resources from the combined resource account to the plurality of users.

In some embodiments, the remaining amount of resources is redistributed based on at least one of an agreement between the plurality of users, a proportional amount of resources provided by each of the plurality of users, and non-financial sub-actions provided by each of the plurality of users.

In some embodiments, the computer readable instructions further comprise instructions for providing a line of resource credit associated with the combined resource account to the second user and the third user; and applying the line of resource credit to the combined resource account.

In some embodiments, the computer readable instructions further comprise instructions for providing a savings product to the second user and the third user, wherein the savings product is configured to establish and grow a base set of resources set aside for addressing the one or more future actions.

In some embodiments, the first amount of resources and the second amount of resources are based on an agreement between the second user and the third user.

Embodiments of the present invention also provide a computer implemented method for linking and managing resources across multiple platforms for distribution to address future actions, said computer implemented method comprising providing a computing system comprising a computer processing device and a non-transitory computer readable medium, where the computer readable medium comprises configured computer program instruction code, such that when said instruction code is operated by said computer processing device, said computer processing device performs the following operations receiving a request, from a computing device of a first user to establish a collaboration for addressing one or more future actions between a plurality of users associated with the first user; transmitting a request, to computing devices of each of the plurality of users, to contribute to the one or more future actions; receiving, from a computing device of a second user, an acceptance from the second user, wherein the acceptance from the second user is associated with an approval to link a resource account of the second user with the collaboration for addressing the one or more future actions; receiving, from a computing device of a third user, an acceptance from the third user, wherein the acceptance from the third user is associated with an approval to link a resource account of the third user with the collaboration for addressing the one or more future actions; identifying a first future action of the one or more future actions; identifying a total resource amount associated with addressing the first future action; in response to identifying the total resource amount associated with addressing the first future action, transmitting a request, to the computing device of the second user, to approve a transfer of a first amount of resources from the resource account of the second user to a combined resource account associated with addressing the first future action; in response to identifying the total resource amount associated with addressing the first future action, transmitting a request, to the computing device of the third user, to approve a transfer of a second amount of resources from the resource account of the third user to the combined resource account associated with addressing the first future action; receiving, from the computing device of the second user, an acceptance to transfer the first amount of resources from the resource account of the second user to the combined resource account; transferring the first amount of resources from the resource account of the second user to the combined resource account; receiving, from the computing device of the third user, an acceptance to transfer the second amount of resources from the resource account of the third user to the combined resource account; transferring the second amount of resources from the resource account of the third user to the combined resource account; and transferring the total resource amount from the combined resource account to one or more merchants associated with the first future action.

In some embodiments, the method further comprises receiving, from a computing device of a fourth user, an acceptance from the fourth user, wherein the acceptance from the fourth user is associated with an approval to link a non-financial sub-action to be performed by the fourth user with the collaboration for addressing the one or more future actions; identifying a need for the non-financial sub-action to be completed to address the first future action; and in response to identifying the need for the first non-financial sub-action to be completed, transmitting a request to the computing device of the fourth user to perform the non-financial sub-action.

In some embodiments, the method further comprises determining that the one or more future actions have been completed; and in response to determining that the one or more future actions have been completed, redistributing a remaining amount of resources from the combined resource account to the plurality of users.

In some embodiments, the remaining amount of resources is redistributed based on at least one of an agreement between the plurality of users, a proportional amount of resources provided by each of the plurality of users, and non-financial sub-actions provided by each of the plurality of users.

In some embodiments, the method further comprises providing a line of resource credit associated with the combined resource account to the second user and the third user; and applying the line of resource credit to the combined resource account.

In some embodiments, the method further comprises providing a savings product to the second user and the third user, wherein the savings product is configured to establish and grow a base set of resources set aside for addressing the one or more future actions.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
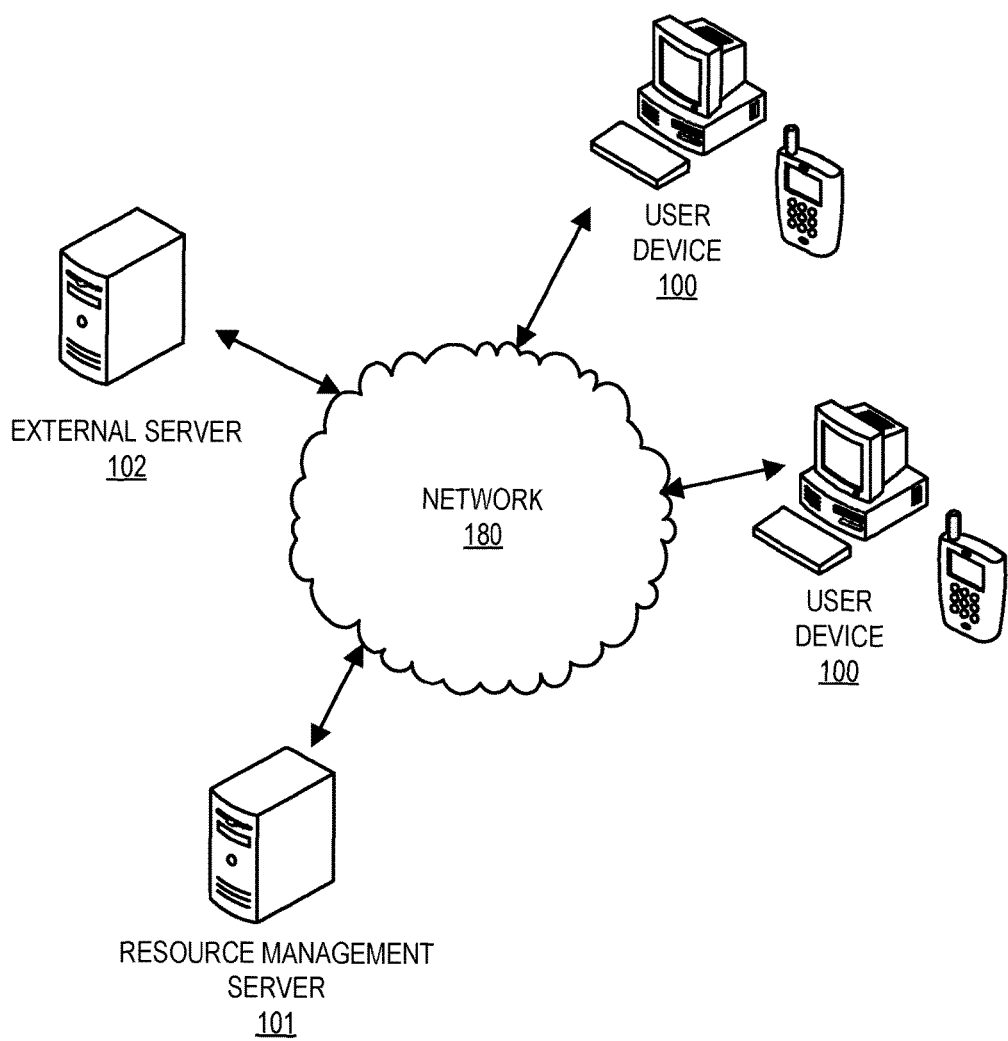
Figure 2:
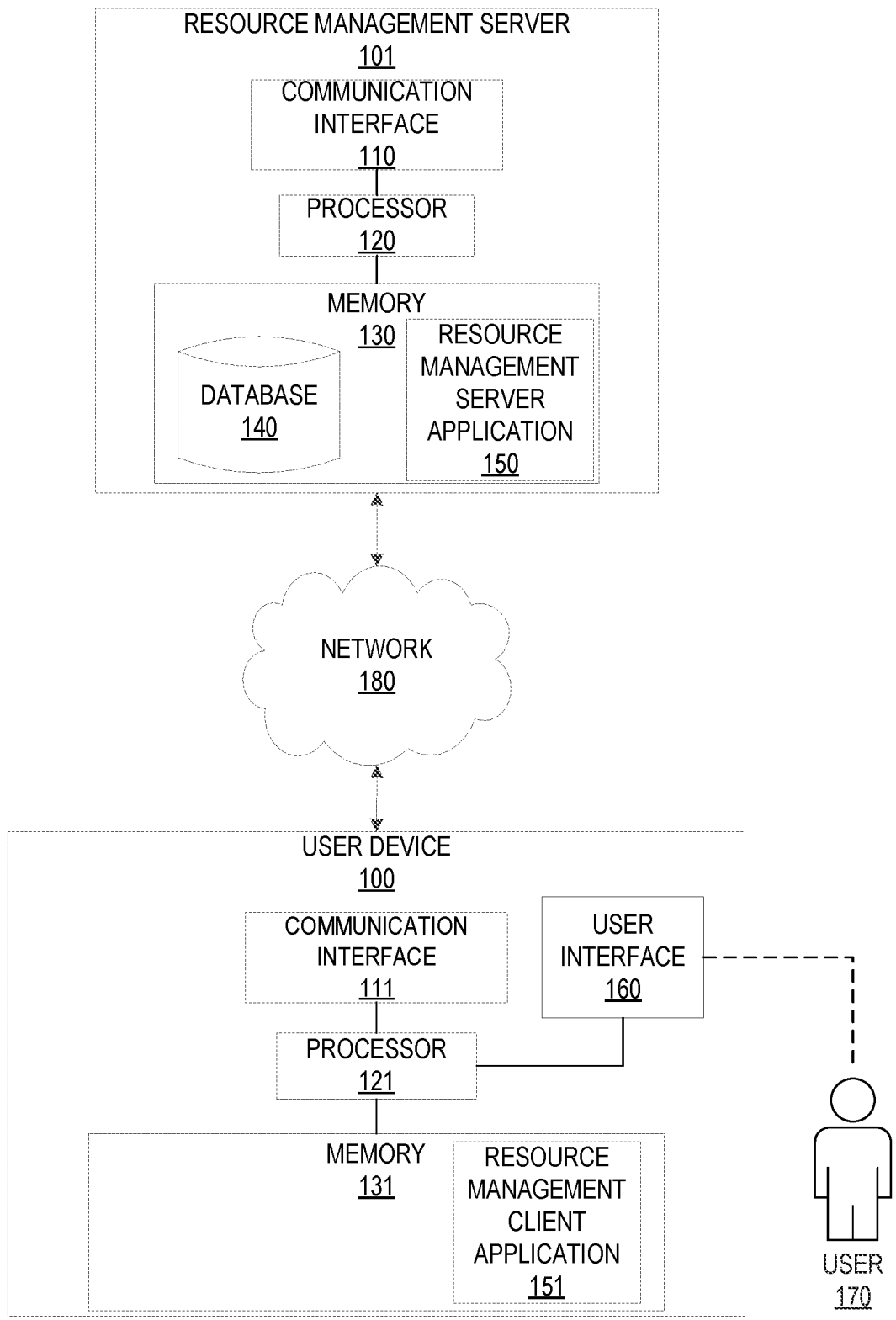
Figure 3:
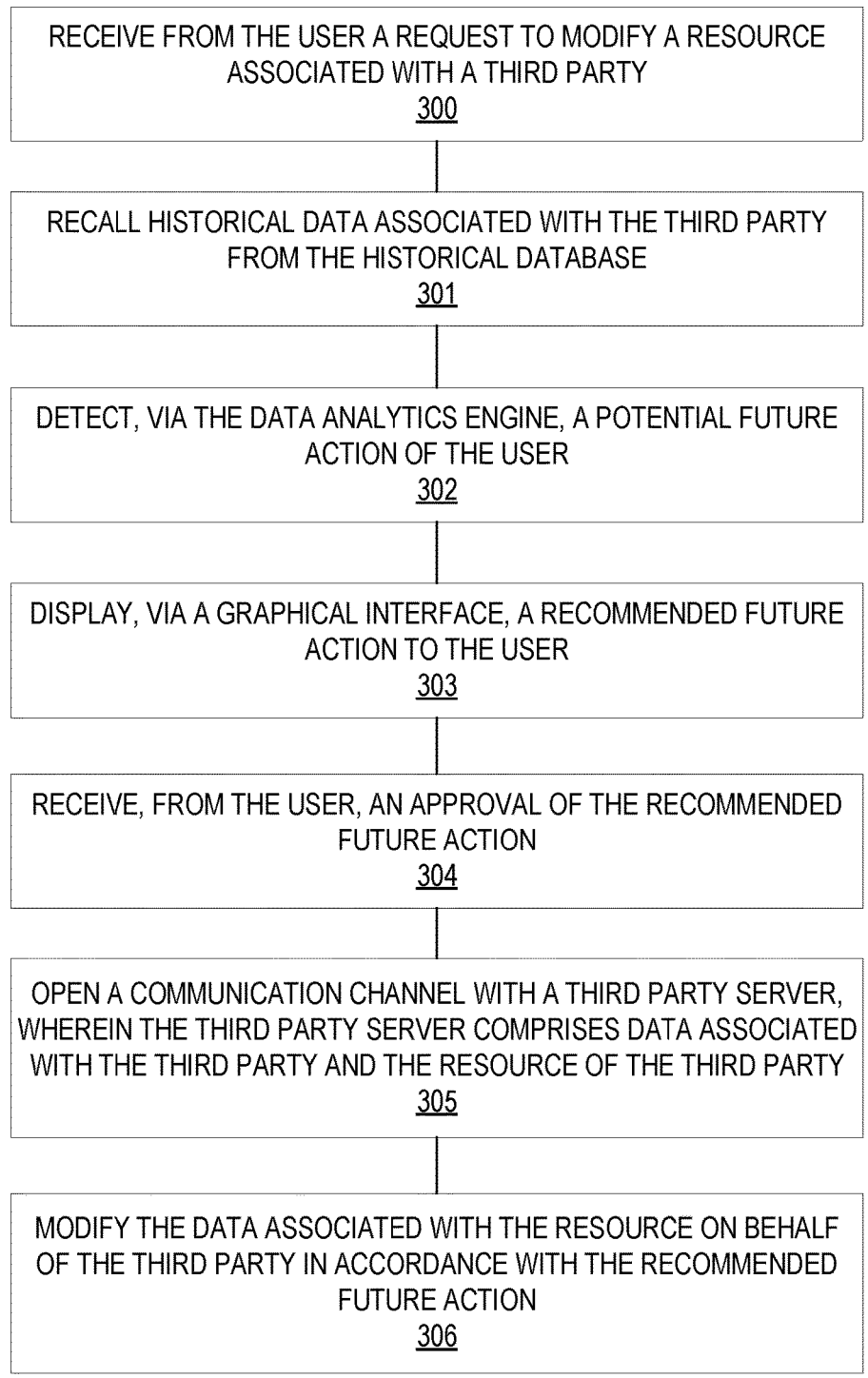
Figure 5:
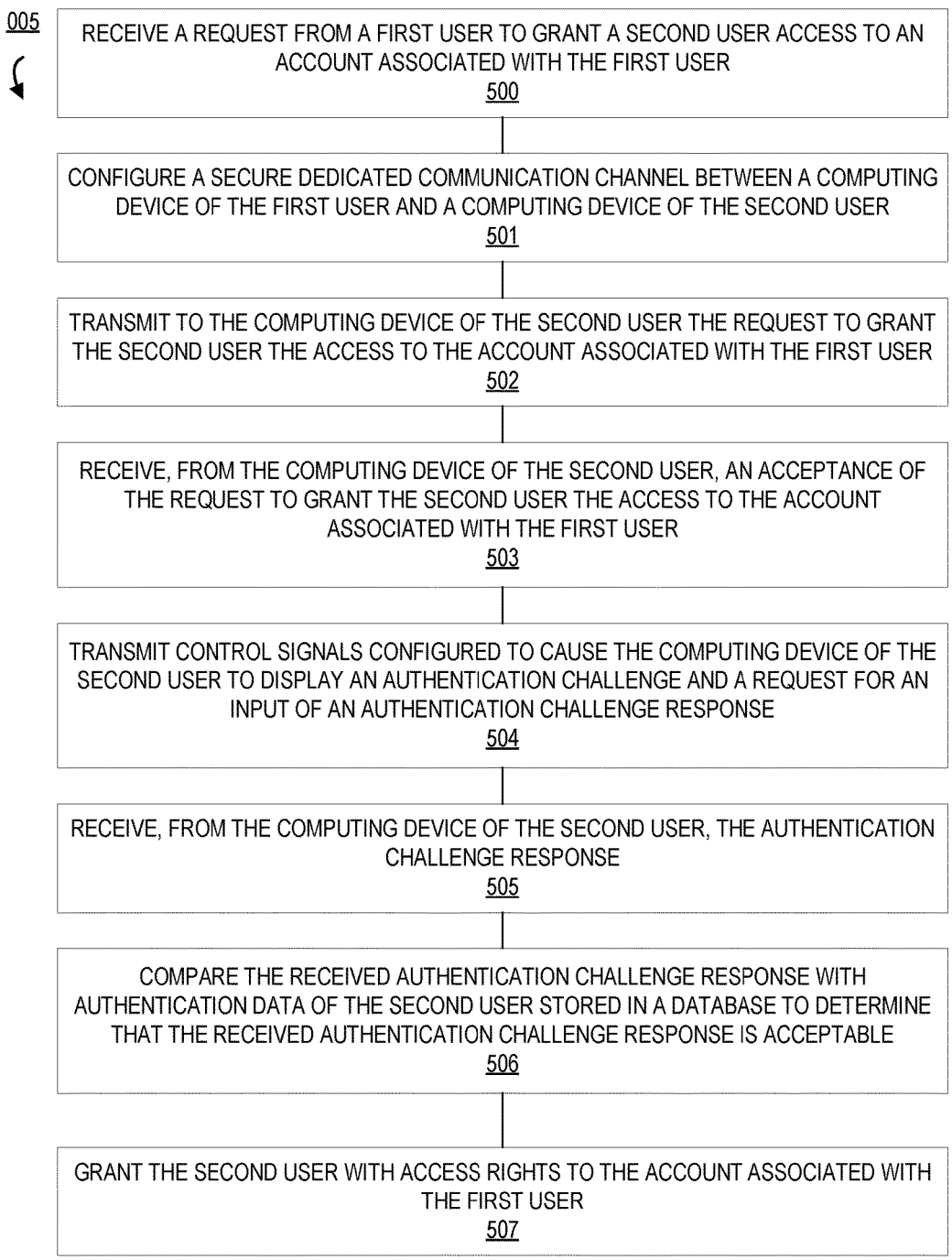
Figure 6:
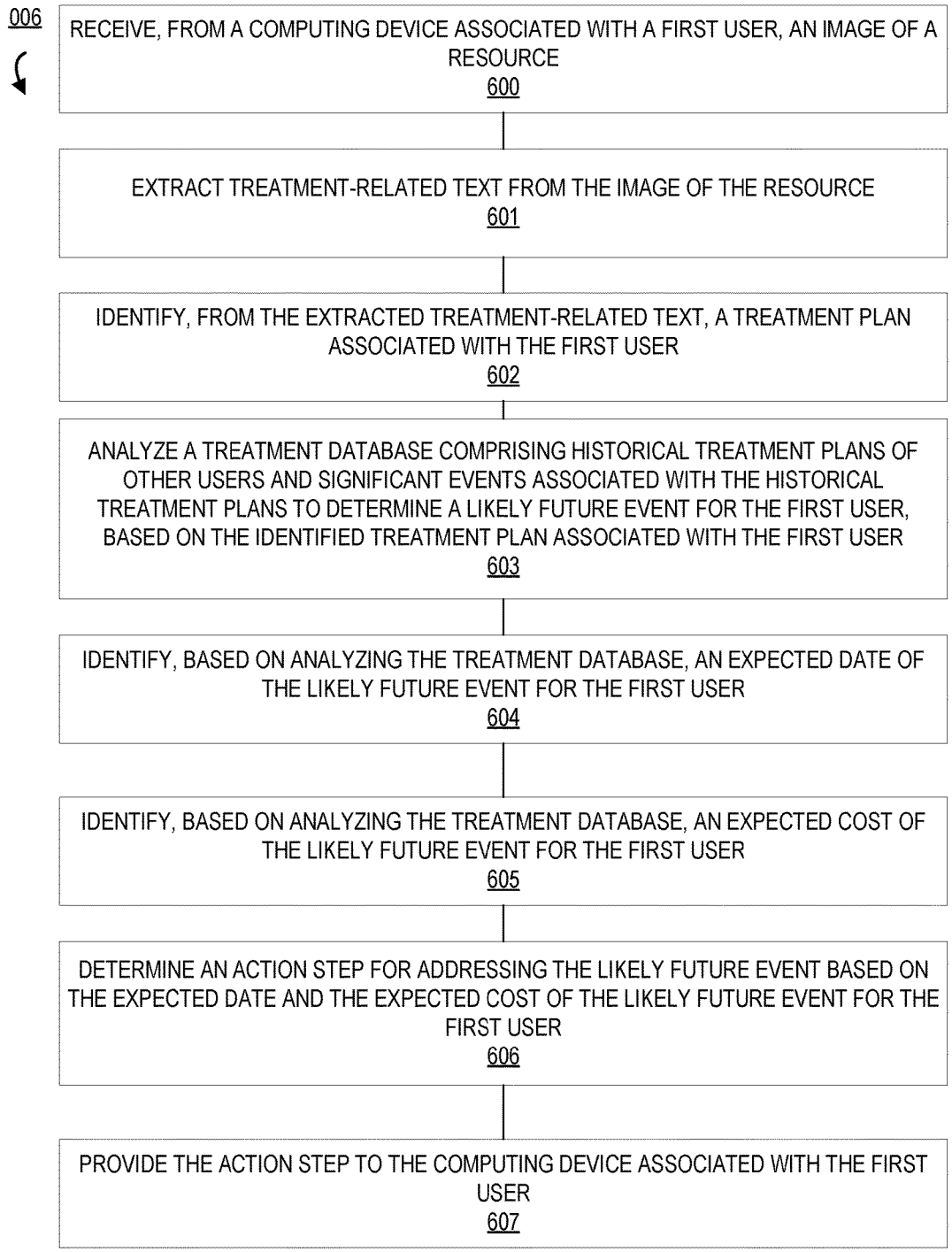

Having thus described embodiments of the invention in general terms, reference will now be made to the accompanying drawings, wherein:

FIG. 1 depicts an operating environment, in accordance with one embodiment of the present invention;

FIG. 2 depicts a schematic of a user device and a resource management server, in accordance with one embodiment of the present invention;

FIG. 3 illustrates a process flow for managing resources, in accordance with one embodiment of the present invention;

FIG. 4 illustrates a process flow for alerting users of a change in status of another user, in accordance with one embodiment of the present invention;

FIG. 5 illustrates a process flow for using a P2P architecture to securely transmit documents between users on behalf of a third party, in accordance with one embodiment of the present invention;

FIG. 6 illustrates a process flow for determining and providing an action step based on captured image data, in one embodiment of the present invention;

FIGS. 7A and 7B illustrate a first and a second part of a process flow for combining resources of a plurality of users, in accordance with one embodiment of the present invention; and FIG. 8 illustrates a process flow for receiving transmissions from disparate nodes and triggering automatic portal action(s), in accordance with one embodiment of the present invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein.

Embodiments of the invention provide for a system that receives transmissions from disparate nodes and triggers automatic portion action. In some embodiments, the system provides for patient self-reporting of status information in order to leverage a caregiver portion action as described herein. In addition to receiving and aggregating data from financial sources, Internet of Things (IOT) sources, patient mobile devices and the like, the system also receive status updates manually from the patient. The system may rely on known information regarding the patient's schedule and timeline to pose questions or suggestions to the patient regarding possible updates. For example, if the time for an appointment has arrived, the portal may push a notification to the patient's mobile device requesting that the patient confirm that the patient has arrived for the appointment. This interaction also provides that patient an easy way to report difficulties or problems by predicting likely problems and requesting confirmation from the patient that they are experiencing the predicted type of problem. Appropriate notifications can then be sent to caregivers and/or additional automatic actions may be taken to mitigate the confirmed problem.

"User" as used herein may refer to an individual or entity that is authorized and authenticated to utilize a system for managing resources as described herein. In some embodiments, the user may be an individual entrusted to manage resources for a third party. In some embodiments, the user may be associated with or related to the third party such that the user is an administrator, manager, operator, or the like.

"Third party" as used herein may refer to an individual or entity for whom or for which resources are managed. Typically, one or more users will use the system to manage resources based on the third party's particular requirements.

"Entity" as used herein may refer to an individual or an organization that owns and/or operates the resource management systems and the associated computing systems. The entity may be a business organization, a non-profit organization, a government organization, and the like.

"User device" as used herein may refer to a computing device used by the user to access the system through an online portal. The user device may include a processor, a non-transitory storage medium, a communications device, and a display. The system may support user logins and inputs from any combination of similar or disparate devices. Accordingly, the user device may be a portable electronic device such as a smartphone, tablet, or laptop, or the user device may be a stationary unit such as a personal desktop computer or a networked terminal within an entity's premises.

"Resource" as used herein may refer to an asset that is managed and/or contributed by the user for the benefit of the third party. Resources may include secured data records, documents, video/audio information, location information, funds, forms, other types of information about or associated with the third party. In some embodiments, the resource may be generated by the system.

"Resource data" as used herein may refer to a data structure that is associated with a particular resource. Resource data is identified, processed, and stored by the system, and may include various types of information associated with the resource, such as file data, metadata, account information, and the like.

"Historical data" as used herein may refer to data collected over a period of time by the system. The historical data may comprise information on resources or resource data, actions taken by the user within the system, the users and the third parties themselves, recurring events associated with the users and/or the third parties, and the like.

Embodiments of the present invention provide a system, computer program product, and method for online management of third-party resources. In particular, the system may gather resource data associated with a particular resource to be managed for a third party. The system then may receive user inputs from one or more users. In some embodiments, the user input is a request to access and/or modify or manage a particular resource on behalf of the third party. In such embodiments, there may exist a particular relationship between the user or users and the third party or third parties. Accordingly, the resource may be audio, video, or location data obtained from an electronic device associated with the third party. In other embodiments, the resource may be a private data record containing information about the third party, such as health care records, insurance records, financial records, legal documents, and the like. In yet other embodiments, the resource may be funds in a special account that are managed by the users on behalf of the third party. In some embodiments, multiple users may be able to manage the resource(s) using the system.

The system may include a data collection module which collects historical data in real-time or near-real time over the course of the system's use. In some embodiments, the historical data may include user inputs and/or actions taken by the user within the system, such as requests to access or manage the resource. In some embodiments, the system may further include a data analytics engine that, based on both historical data and data provided by the users in real time, predicts future requests to manage resources initiated by the one or more users. For instance, the system may collect data on past requests to manage resources for the third party, the third party's biographical data, the third party's schedule, the relationships between the third party and the one or more authorized users, and the like. Based on this data, the system may determine what actions the users are likely to take within the system with respect to any given third party.

In some embodiments, the user or users may have a special relationship with the third party for whom resources are managed, such as employee-employer, parent-child, caregiver-patient, and the like. The system may allow the user to manage resources on behalf of the third party, such as by scheduling appointments, generating documents or records, or contributing/managing funds in a designated account. The system may further allow the user to request resource data regarding the third party, such as location information (e.g. GPS coordinates), audio/video from the third party's mobile device, or medical information, or any other such information the user may use to provide service or care to the third party.

In some embodiments, the system may include an online portal which serves as the interface between the system and the users. The system may run its processes on a server or network of servers which users may access using a computing device. In some embodiments, the system may provide to the user a client application or program which is used to access the server-side application over a network. The online portal may present a graphical interface to the display of the user device, through which the user may select from a number of tools and functions provided by the system. For instance, the system may provide tools that allow one or more users to access or manage resources or resource data.

The graphical interface may include a number of panels which may receive inputs or display information to the user. For example, the graphical interface may include a resource management panel, which allows the user to manage the resource through the system. The resource management panel may contain buttons or areas that receive user input related to the resource to be managed, such as text entry boxes, clickable buttons, check boxes, or radio buttons. The resource management panel may further include tools to help the user manage resources, such as a text editor, a scheduler, financial account management tools, and the like. The graphical interface may further include a resource viewing panel, which displays various types of resource data to the user. For instance, the resource viewing panel may be configured to display text files, documents, calendars, video/audio files, maps and location data, images and photos, and the like. In some embodiments, the graphical interface may also be configured to allow the third party to view and/or manage resources through the system. The system may selectively restrict the third party's use such that the third party may only elect to use certain functions within the resource management panel or may only view certain types of resource data within the resource viewing panel. In other embodiments, the third party may be precluded entirely from accessing the system.

The graphical interface may also include a notifications panel, through which the system provides recommended actions to the user based on the data collected and analyzed by the data analytics engine. The recommendations displayed in the notifications panel may further contain a clickable or selectable link which the user may use to directly access the recommended action. For example, the system may, based on historical data, recognize that a user uses the system to schedule an appointment for the third party on a regular basis. The system may then provide a recommended action to the user through the notifications panel, which may contain a link to automatically schedule the appointment. It should be noted that the system may further track the user's response to the recommended actions to further add to historical data. In this way, the system may, through machine learning, adapt to the needs of the user and the associated third party on a case-by-case basis, allowing the user to efficiently manage or view resources.

In some embodiments, the system may be owned or operated by an entity. In such embodiments, the entity may employ additional computer systems, such as authentication servers, to validate and certify resources inputted by the plurality of users within the system. The system may further establish different levels of authentication and/or authorization for multiple users associated with a particular third party, such that a primary user may be authorized to utilize more functions than secondary users. The system may further provide an authentication method to the third party, who may access the online portal in a limited manner.

The system addresses a number of computer technology-centric challenges as described above. As noted, the system is typically configured to dynamically provide recommended future actions to the user based on the output of the data analytics engine. By dynamically predicting and recommending future actions, the system is able to short-circuit intermediate actions that the user would have otherwise had to take within the interface. By avoiding these intermediate actions, the system is able to increase computing efficiency and thereby reduce demands on computer resources such as processing power, memory space, storage space, cache space, electric power, and networking bandwidth.

In an exemplary embodiment, one or more users (e.g. caregivers) may use the system to provide management and care to a third party (e.g. a patient). For instance, said caregivers may be the family members of an elderly patient who requires day-to-day care. To provide care to the patient, the caregivers may log into the online portal to access the resource management system, wherein they may make use of a variety of tools. For instance, the portal may allow caregivers to access the patient's healthcare records, insurance records, bills, and the like. In such a case, the system may facilitate the steps necessary for caregivers to provide care to the patient, such as arranging for payment of bills, insurance, and scheduling of medical appointments. The system may further automatically generate a power of attorney form should the patient become unable to competently manage his or her own affairs. In some embodiments, the caregivers may manually use the online portal to generate the power of attorney form. In other embodiments, the system may automatically suggest the generation of the power of attorney form to the caregivers based on historical and projected data associated with the patient, such as health status, current or future treatment, biographical information such as age or sex, or family history of medical conditions.

In embodiments in which multiple caregivers log into the online portal, the system may apportion duties to the multiple caregivers based on a number of factors, such as relationship to the patient, geographic location in relation to the patient, financial ability to assist the patient, time schedules, and the like. The system may be configured to send notifications to the user devices of the multiple caregivers to remind each caregiver of his or her individual duties. In some embodiments, the notification may be sent through an application on the user device. The system may also list the duties, the status of the duties, and the assigned caregiver for each duty for all related caregivers to view. Accordingly, in some embodiments, the system may apportion duties amongst multiple caregivers to pay for the care of the patient. The duties to pay may be determined by the system based on predetermined agreements for payment. In some embodiments, the system may track financial data of each caregiver, such as income, liabilities, and the like, to suggest an optimal portion for each caregiver to contribute. For instance, the system may arrange for the payment of a medical procedure for the patient by requesting funds from each caregiver according to the predetermined agreements for payment. In some embodiments, in addition to arranging for payment of specific instances of care, the system may allow caregivers to contribute to a savings plan to provide care to the individual.

In some embodiments, the system may further allow the patient to log into the online portal. In such an embodiment, the caregivers may limit the types of information that is shown the patient or alter the information itself. For instance, the caregiver may choose to obfuscate savings account information or replace some of the account information, such as account balance, with dummy values.

The system may also provide a way for caregivers to track the patient's location and receive video and audio data from the patient's mobile device. In such an embodiment, the patient's mobile device may be a cellular phone, internet-of-things device, wearable device, personal security device, and the like. The mobile device may be equipped to transmit video and audio data to be viewed through the online portal to ensure that caregivers may access the patient's location and health status. In some embodiments, the system may further be configured to detect and identify the types of medication being taken by the patient. In some embodiments, this may be achieved by running optical character recognition (OCR) algorithms on image or video data received through the patient's mobile device. The algorithm may detect drug names from the label of a drug container in the patient's possession. In other embodiments, the mobile device may use other recognition methods, such as barcodes or QR codes to identify the medication being used by the patient. In yet other embodiments, an internet-of-things device may be used to transmit drug counts independently of the label. For instance, an internet-of-things pill bottle may be able to count the number of pills remaining within the bottle. Once the number of pills falls below a certain threshold, the system may automatically place an order with the patient's pharmacy to refresh the supply of the drug in question. In some embodiments, multiple mobile devices may be installed in various locations of the patient's home, which would thereafter be tracked by the system. Each mobile device may be configured to transmit real-time data to the system on an on-demand basis or continuous basis. In this way, the system provides a method for caregivers to obtain real-time data to provide care to the patient while simultaneously allowing the patient to have a degree of independence and privacy. In some embodiments, the system may also allow caregivers to obtain video and audio data from the patient's device when the patient is receiving medical care, to provide caregivers with a "virtual-reality" means to participate in the medical appointments.

In some embodiments, once the system has identified the drugs being taken by the patient, the system may identify dosage data to assist caregivers in ensuring that the patient consumes the correct amount of the drug. In some embodiments, the system may further identify drug interactions between the medications being currently taken by the patient or medications that will be prescribed in the future, in order to warn the caregivers and/or the patients of adverse interactions and side effects. The system may further use aggregated data to identify next steps, such as procedures or drugs to be recommended in the future, and provide notifications of the suggestions to the caregivers. The aggregated data may comprise data associated with other individuals of a similar biographical info (e.g. age, sex, weight) and medical diagnosis (e.g. specific illness, drugs, procedures) to help identify the recommended next steps. The system may then recommend an optimal location to receive the drugs or procedures based on a number of factors, such as insurance coverage, geographic location, cost, quality of care, or the like.

The system may also utilize a person-to-person (P2P) authentication method to securely transmit sensitive information between caregivers and/or the patient. Such information may include medical documents, prescriptions, power of attorney forms, and the like. The P2P system may further be used to obtain authorization from the patient for the generation of such documents.

FIG. 1 is a block diagram illustrating an operating environment 001, in accordance with one embodiment of the present invention. The operating environment may include a plurality of user devices 100 in operative communication with a resource management server 101 over a network 180. The network 180 may also be a global area network (GAN), such as the Internet, a wide area network (WAN), a local area network (LAN), or any other type of network or combination of networks. The network 180 may provide for wireline, wireless, or a combination wireline and wireless communication between devices on the network 180. The user device may be a mobile device such as a smartphone, tablet, or laptop, a personal computing device such as a desktop computer, smart device, single board computer, or a device owned and operated by an entity, such as a computer system terminal located on the entity's premises. The resource management server 101 is responsible for running the resource management application and running its various processes. It should be understood that the resource management server 101 as depicted herein may be embodied in a single server or multiple servers distributed over varying geographic distances.

Generally, the user devices 100 are used to log onto the resource management server 101 over the network 180 to access the online portal (e.g., over a secure communication channel). The resource management server 101 may require that authentication credentials are provided by the user device 100. In some embodiments, the authentication credentials may include a username, password, a biometric identifier, a cryptographic key, a token, and the like. The resource management server 101 may further require that more than one authentication credential is provided as parts of a multi-step authentication process. Once the user has been authenticated, the user may log onto the online portal on the resource management server 101 using the user device 100 to access the resources and resource management tools therein.

In some embodiments, the operating environment may further include a external server 102 which may be in operative communication with the user device 100, the resource management server 101, or both, over the network 180. The external server 102 may contain data associated with the user which may be accessed by some of the resource management tools run on the resource management server 101. This configuration allows the resource management server 101 to automatically pull the data associated with the user from the external server 102 in order to run its various processes. For example, the external server 102 may contain data relating to the third party's financial accounts, medical records, legal documents, and the like, while the resource management server 101 may provide tools to manage said data. In such an embodiment, the user may provide a second set of authentication credentials associated with the user's financial account to the external server 102 directly. Alternatively, the user may store the second set of authentication credentials on the resource management server 101, which may then use said authentication credentials to access the data within the external server 102.

FIG. 2 is a block diagram illustrating the resource management server 101 and the user device 100 in more detail, in accordance with one embodiment of the present invention. The resource management server 101 typically contains a processor 120 communicably coupled to such devices as a communication interface 110 and a memory 130. The processor 120, and other processors described herein, typically includes circuitry for implementing communication and/or logic functions of the server 101. For example, the processor 120 may include a digital signal processor device, a microprocessor device, and various analog to digital converters, digital to analog converters, and/or other support circuits.

The resource management server may use the communication interface 110 to communicate with other devices over the network 180. The communication interface 110 as used herein may include an Ethernet interface, an antenna coupled to a transceiver configured to operate on a cellular data or WiFi signal, and/or a near field communication ("NFC") interface.

The resource management server may include a memory 130 operatively coupled to the processor 120. As used herein, memory includes any computer readable medium (as defined herein below) configured to store data, code, or other information. The memory may include volatile memory, such as volatile Random Access Memory (RAM) including a cache area for the temporary storage of data. The memory may also include non-volatile memory, which can be embedded and/or may be removable. The non-volatile memory can additionally or alternatively include an electrically erasable programmable read-only memory (EEPROM), flash memory or the like.

Typically, a resource management server application 150 is stored within the memory 130 to implement the functions of the online portal through the processor 120 on the resource management server 101. The resource management server application 150 allows a user 170 to connect to the resource management server 101 through a user device 100, in order to access the resource data therein as well as utilize the resource management tools provided through the online portal. The resource management server application 150 includes the logic code portions to determine the appropriate recommended user actions as well as the code portions to collect usage and historical data from the plurality of users 170 within the system.

The memory 130 may further include a database 140 containing data to be processed and/or manipulated by the resource management server application 150. The database 140 may contain usage and historical data provide by the users 170. The database 140 may also contain data on the various classifications to be used to categorize the resources and the users, on what classifications correspond to which resources, as well as logical links between and amongst the various resources and the users. It should be understood that while the database 140 is depicted as a single unit within a single resource management server in FIG. 3, the database 140 may represent multiple databases implemented across multiple resource management servers 101. It should also be understood that the resource management server application 150 may implemented in a distributed manner amongst a plurality resource management servers 101. The database 140 may also be stored on a separate, distinct memory 130 from the resource management server application 150.

The user device 100 typically also includes a processor 121 operatively coupled to a communication interface 111 and a memory 131. The memory 131 typically stores a resource management client application 151, which causes the processor 121 to display a user interface 160 to the user 170. It should be understood that the display on which the user interface 160 is presented may include an integrated display (e.g. a tablet or smartphone screen) within the user device 100, or an external display device (e.g. a computer monitor or television). The resource management client application 151 establishes a connection with the resource management server application 150 over the network 180 to allow the user 170 to access the various functions of the system. In particular, the resource management client application 151 receives inputs from the user interface 160, which may include such inputs as user authentication credentials, requests to view resource data, requests to utilize the resource management tools of the resource management server application 150, and the like.

In a typical embodiment of the invention, the user 170 accesses the resource management client application 151 through the user interface 160. The resource management client application 151 sends a request over the network 180 to establish a communication link with the resource management server 101 through the resource management server application 150. Upon receiving the request, the resource management server application 150 causes the resource management server 101 to send a command to the user device 100 to prompt the user 170 for authentication credentials through the user interface 160. Upon receiving authentication credentials from the user 170, the resource management client application 151 sends the authentication credentials to the resource management server application 150. Upon successful authentication, a communication link between the resource management client application 151 and the resource management server application 150 is established. The user 170 then provides a request to manage a resource to the resource management client application 151, which then sends the request to the resource management server application 150. The resource management server application 150 then provides resource management tools to the user through the graphical user interface 160, through which the user 170 may take a number of actions to benefit the third party.

The system may store user activity data within the online portal within the database 140. In some embodiments, the resource management server application 150 may cause the processor 120 to periodically query the user device 100 to obtain snapshots of the state of the resource management client application 151. Upon receiving the query, the resource management client application 151 immediately obtain a snapshot of user actions taken within the graphical interface, then send the snapshot to the resource management server 101. In other embodiments, the resource management client application 151 may continuously track user inputs and temporarily store them in the memory 131, then send the history of user inputs to the resource management server 101 upon receiving the query. In other embodiments, the resource management client application 151 may periodically track the user's inputs and push the input data to the resource management server 101 without waiting to receive a query.

FIG. 3 illustrates a process flow 003 for managing resources, in accordance with one embodiment of the present invention. The process begins at block 300, where the system receives from the user a request to modify a resource associated with a third party. In one embodiment, the user may be a caregiver of a third party patient. In such an embodiment, the user may utilize the various functions of the system to manage resources associated with the user to enable the user to efficiently provide care to the third party. For instance, the user may contribute and/or manage funds to be used for the purpose of caring for the third party. In some embodiments, the user may use the system to automatically generate legal documents required to facilitate the third party's care, such as a power-of-attorney form. The system may further allow the user to schedule medical appointments or view video/audio data or location data for the third party.

The process continues to block 301, where historical data associated with the third party is recalled from the historical database. The historical database may contain a number of different data records related to the third party, such as medical history, previous funds spent on caregiving, legal status of affairs, as well as previous instances in which the system was used to provide management of resources for the care of the third party.

The process continues to block 302, where the system detects a potential future action of the user via the data analytics engine. The data analytics engine uses the historical data within the historical database to predict what the user intends to request of the system. For instance, the historical data may indicate that medical appointments have historically been scheduled at the beginning of the month. Based on this data, the data analytics engine may predict that the user intends to schedule such an appointment upon signing on to the system.

The process continues to block 303, where a recommended future action is displayed to the user via a graphical interface. In some embodiments, the user may be notified of the recommended future action by the notifications panel. In an exemplary embodiment, the user may receive a recommendation to schedule the medical appointment on behalf of the third party. The displayed notification may contain a clickable button which allows the user to directly access the scheduling interface.

The process continues to block 304, where the system receives an approval of the recommended future action from the user. The system may execute its processes to carry out the recommended future action on behalf of the user. In this way, the system efficiently prevents the need for the user to spend time and technical resources to manually find the relevant tools to conduct management of resources for the care of the third party. The system may further add a record of the approval of the recommended future action to the historical database, which may serve as a positive indicator of the degree to which the data analytics engine is accurately predicting intended future acts of the user.

The process continues to block 305, wherein the system opens a communication channel with an external server, wherein the external server comprises data associated with the third party and the resource of the third party. In some embodiments, the external server may be operated by an entity such as a hospital, wherein the external server contains medical information about the third party (e.g. the patient), such as current medications, current treatments, scheduled appointments, treatment plans, and the like. The system may then download the medical data to decide on a recommended course of action for the patient. For instance, the system may recommend that the caregiver schedule an appointment for a doctor's visit and/or medical procedure in accordance with the downloaded medical data. The system may then set up communications with the external server to allow caregivers to automatically execute the desired future action (e.g. set up an appointment).

The process concludes at block 306, where the system modifies the data associated with the resource on behalf of the third party in accordance with the recommended future action. In an exemplary embodiment, the system may communicate with the external server to automatically schedule an appointment for the patient. The information needed to schedule the appointment may be populated using the historical medical data as well as caregiver input.

FIG. 4 illustrates a process flow 004 for alerting users of a change in status of another user, in accordance with one embodiment of the present invention. The process begins at block 400, where the system provides a responder application to one or more users associated with a first user for installation on remote computing devices of the one or more users. In an exemplary embodiment, the responder application may be an application that connects to the online portal. The one or more users may be the caregivers of a first user, who is a third party patient. The one or more caregivers may use the responder application on their respective remote computing devices to log into the online portal to provide care for the third party.

The process continues to block 401, where the system continuously monitors a computing device associated with the first user for an indication of a status change for a status of the first user. For instance, the status change for a status of the first user may be a change in health status information (e.g. heart rate, breathing rate, activity level, body position, etc.), physical location, movement, consumption of medication, and the like. The computing device associated with the first user may be a mobile device such as a cellular phone, or a wearable "smart" device that is configured to detect the status changes and communicate them wirelessly to the system. The computing device may further be configured to transmit video and audio data to the system to allow the caregivers to receive the data through the online portal to provide remote care to the patient. In some embodiments, multiple computing devices associated with the first user may be installed throughout the first user's residence in addition to the computing device kept on the first user's person. The computing devices may be configured to send status changes and/or video and audio data to the system only when a change in status necessitates intervention from the caregivers, such as a sudden and drastic increase in heart rate or breathing rate that may be indicative of an injury or acute illness. In some embodiments, the computing devices may be configured to send status changes only during certain time periods. In this way, the privacy of the first user is preserved while simultaneously allowing the caregivers to maintain open communications with the first user to provide care.

The process continues to block 402, where the system identifies, from the computing device associated with the first user, the indication of the status change for the first user. In some embodiments, the system may be configured to constantly query the computing device over the network. In other embodiments, the computing device associated with the first user may be configured to periodically send updates to the system over the network. As stated previously, the computing device may further be configured to push an update to the system upon detecting a status change that may be classified as an emergency.

The process continues to block 403, where the system, in response to identifying the indication of the status change for the first user, identifies a responsive action associated with the status change of the first user. In an exemplary embodiment, the patient may have run out of a particular medication. The computing device may read the label on the pill bottle using OCR to determine drug information such as chemical composition, dosage, and pill count. Based on the pill count and dosage, the computing device may report to the system that the appropriate responsive action is to reorder a new bottle of the medication. The system may at this point detect that a prescription must be renewed, and subsequently automatically generate the documents necessary to authorize a prescription renewal. In another exemplary embodiment, the patient may have collapsed from a sudden onset of illness or by accident. Upon detecting a drastic change in medical status, the system may determine that the appropriate responsive action is to automatically request emergency service. The system may use the various types of historical data relating to the patient to submit a request for emergency services. In other embodiments, the system may determine that the appropriate responsive action is to notify caregiver of the change in status so that the caregiver may provide assistance on site.

The process concludes at block 404, where the system in response to determining the responsive action, transmit a responsive action alert over a wireless communication channel to a mobile computing device of a second user of the one or more users. In an exemplary embodiment, the patient may be running low on a particular medication. The system may reorder the medication and send an alert to a second user (e.g. the primary/administrative caregiver) to notify the second user that the medication has been ordered. In another embodiment, the system may send an alert to the second user that emergency services have been called to the patient's location. The system may, through the computing device associated with the first user, continuously track the status of the patient during transportation to the emergency center and alert the second user with information about the emergency center, such as the name of the establishment, location, contact information, and the like. In some embodiments, the system may utilize commercial transportation services to transport the patient to a medical center. In such an embodiment, a mobile device carried by the patient may constantly communicate with the system to push updates about the patient's current location to the online portal and/or the caregivers until the patient arrives at the medical center. In another embodiment, a designated caregiver may be assigned to transport the patient to a medical center. If the designated caregiver cannot be reached, the system may automatically notify the next caregiver on a list of emergency contacts until a caregiver is successfully contacted.

FIG. 5 illustrates a process flow 005 for using a P2P architecture to securely transmit documents between users on behalf of a third party, in accordance with one embodiment of the present invention. The process begins at block 500, where the system receives a request from a first user to grant a second user access to an account associated with the first user. In an exemplary embodiment, the first user (e.g. a patient) may wish to grant financial/medical account access to the first user (e.g. a caregiver). Once the second user obtains the right to access the patient's accounts, the system may allow the second user to conduct a number of actions, such as transfer treatment documents, prescriptions, power of attorney forms, funds, and the like. The system may use P2P authentication technology to verify the identities of the first user and the second user by their respective computing devices. In particular, the system may query the data stored on the computing device, such as name, address, phone number, IMEI, ESN, and the like, and compare the queried data with the stored data within the system's databases. In this way, the system may authenticate the first user and the second user in a separate manner from the username and password authentication scheme. In some embodiments, the system may require the querying of data in addition to the username and password authentication scheme.

The process continues to block 501, where the system configures a secure dedicated communication channel between a computing device of the first user and a computing device of the second user in response to receiving the request from the first user. At this step, the system uses an encrypted channel to establish a link between the computing devices of the patient and the caregiver.

The process continues to block 502, where the system transmits, to the computing device of the second user, the request to grant the second user access to the account associated with the first user via the secure communication channel. At this step, the system may cause an alert to appear on the caregiver's device which notifies the caregiver that the patient has requested the caregiver to accept access to the patient's accounts. The caregiver may either accept or decline the request using the inputs on the computing device.

The process continues to block 503, where the system receives, from the computing device of the second user, an acceptance of the request to grant the second user the access to the account associated with the user. At this step, the caregiver has accepted the request and has agreed to manage the patient's accounts in part or in whole as the situation dictates.

The process continues to block 504, where the system transmits control signals configured to cause the computing device of the second user to display an authentication challenge and a request for an input of an authentication challenge response. At this step, the system attempts to verify the identity of the caregiver. In some embodiments, the authentication challenge is a notification that the application wishes to query the caregiver's computing device, and the authentication challenge response is an authorization of the application to query the computing device. In other embodiments, the authentication challenge may be a series of questions selected that only the caregiver may reliably answer, and the authentication challenge response may be the set of answers corresponding to the questions posed by the system.

The process continues to block 505, where the system receives, from the computing device of the second user, the authentication challenge response. The computing device may be configured to transmit the authentication challenge response securely over the network.

The process continues to block 506, where the system compares the received authentication challenge response with authentication data of the second user stored in a database to determine that the received authentication challenge response is acceptable. In an exemplary embodiment, the system may compare the extracted data from the computing device with the historical data associated with the caregiver obtained from the system's databases. The system may, based on the types of data queried, accept a response that matches the historical data within a certain threshold. For instance, receiving name or address data from the computing device may require the system to allow for slightly alternate spellings or abbreviations from what has been stored in the databases. For other types of extracted data, such as IMEI or ESN, the system may require a 100% match between the extracted data and the historical data in order to authenticate the caregiver.

The process concludes at block 507, where the system grants the second user with access rights to the account associated with the first user. At this stage, the second user has been authorized to manage the patient's account on the patient's behalf. Accordingly, the system may automatically generate the power of attorney forms necessary for the caregiver to act on the patient's behalf in a legal capacity. The system may also allow the caregiver to manage funds and medical appointments, as described above.

FIG. 6 illustrates a process flow 006 for determining and providing an action step based on captured image data, in one embodiment of the present invention. The process begins at block 600, where the system receives, from a computing device associated with a first user, an image of a resource. In an exemplary embodiment, the first user is a patient receiving care from one or more caregivers. The resource may be a document that contains information related to the patient's ongoing medical treatment. In some embodiments, the resource may be a container of medicine. The image may be captured using a camera integrated into the patient's computing device.

The process continues to block 601, where the system extracts treatment-related text from the image of the resource. In an exemplary embodiment, the treatment-related text may be information about a drug that can be found on a label, such as drug name, chemical composition, dosage information, pill count, prescribed instructions, primary physician/hospital, pharmacist/pharmacy, and the like. The system may use OCR technology, barcodes, QR codes, and the like to recognize the types of drugs that the patient is currently taking under a treatment plan. In this way, the system may accurately determine not only what the patient has been prescribed but the amount and frequency with which certain drugs are actually being consumed. In some embodiments, the system may collect the treatment-related text to determine compliance by the patient with a treatment plan. In such an embodiment, the patient may use such data to, for instance, lower insurance premiums based on healthy habits.

The process continues to block 602, where the system identifies, from the extracted treatment-related text, a treatment plan associated with the first user. For example, the system may correlate all of the drugs and dosages that the patient is currently taking to analyze drug interactions. The system may, using data analytics, recommend the addition or subtraction of certain drugs from the patient's regimen based on similarly situated patients who are taking the same types of drugs. The system may further track doctor's visits or procedures and correlate them with those of other similar patients to determine an optimal treatment plan according to the patient's need, such as longevity, comfort, etc.

The process continues to block 603, where the system analyzes a treatment database comprising historical treatment plans of the other users and significant events associated with the historical treatment plans to determine a likely future event for the first user, based on the identified treatment plan associated with the first user. The treatment database may comprise information collected by the data analytics from all patients within the system. The system may track the history of each patient within the system and use the aggregated data to predict events and outcomes from the treatment plan of each patient. Once an optimal treatment plan has been determined, the system may examine historical treatment data of other similar patients to calculate an expected timeline of treatment. For instance, the system may determine that the patient will soon need a particular operation or to begin a new method of therapy or drug.

The process continues to block 604, where the system identifies, based on analyzing the treatment database, an expected date of the likely future event for the first user. For instance, the system may determine that the patient will need a particular operation within a specified time frame. The system may then query healthcare providers in the area to identify the best locations for the operation. The best location may be determined based on insurance coverage, geographic location, cost, scheduling, quality of care, specialty in treating the patient's condition, and the like. For instance, the system may examine the patient's finances and insurance status each year, such as how much of the deductible has been met, the cash inflow and outflow, and the like. The system may determine a best location based on regional, cultural, or environmental factors. For instance, the availability or efficacy of treatment may vary based on a region's climate or concentration of specialty providers within a particular area.

The process continues to block 605, where the system identifies, based on analyzing the treatment database, an expected cost of the likely future event for the first user. The system may, using data analytics, determine the average cost of the procedure needed by the patient based on patients receiving the procedure who are similarly situated and live in a similar geographic area. The system may further refine this number based on the queried data obtained from the healthcare providers in the patient's area. In this way, the system not only ensures that the patient will pay a fair price for future procedures, but also provides a way for patients to dispute overly wasteful spending or excessive charges for procedures that were conducted before the patient and/or the caregivers began utilizing the system.

The process continues to block 606, where the system determines an action step for addressing the likely future event based on the expected date and the expected cost of the likely future event for the first user. For example, based on the expected date and cost of the medical procedure, the system may determine a specific doctor and specific hospital with whom to schedule an appointment as an "action step."

The process concludes at block 607, where the system provides the action step to the computing device associated with the first user. The system may send an alert to the computing device associated with the first user that scheduling the procedure with the specific doctor and hospital is recommended. In some embodiments, the alert may be sent to the computing device associated with a second user (e.g. a caregiver), where the caregiver has the power of attorney to schedule appointments on the patient's behalf. The alert may comprise a link that allows the caregiver to schedule the appointment according to the identified treatment plan.

FIGS. 7A and 7B illustrate a first and a second part of a process flow 007 for combining resources of a plurality of users, in accordance with one embodiment of the present invention. Looking now to FIG. 7A, the process begins at block 700, where the system receives, from a computing device of a first user, a request to establish a collaboration for addressing one or more future actions between a plurality of users associated with the first user. In an exemplary embodiment, the first user may be a patient who wishes to create a shared account to be used in providing care to the patient by the plurality of users (e.g. the patient's caregivers). For instance, the system may allow the caregivers to split duties and responsibilities for providing funding for a future action related to the care of the patient, such as a doctor's appointment or medical procedure to be undertaken in the future.

The process continues to block 701, where the system transmits, to the computing devices of each of the plurality of users, a request to contribute to the one or more future actions. At this step, the system sends a requests to the caregivers to contribute funds to cover a portion of the expected cost of the future action. The system may suggest an optimal proportion of funds for which each caregiver will be responsible based on each caregiver's level of income, relationship to the patient, and the like. In other embodiments, the proportion of funds to be contributed may be determined based on a predefined agreement between or amongst the caregivers.

The process continues to block 702, where the system receives, from a computing device of a second user, an acceptance from the second user, wherein the acceptance from the second user is associated with an approval to link a resource account of the second user with the collaboration for addressing the one or more future actions. The second user may be a caregiver of the patient who has accepted the linking of his or her financial account with the collaboration (e.g. the shared fund to pay for medical expenses).

The process continues to block 703, where the system receives, from a computing device of a third user, an acceptance from the third user, wherein the acceptance from the third user is associated with an approval to link a resource account of the third user with the collaboration for addressing the one or more future actions. The third user may also be a caregiver of the patient who has accepted the linking of his or her financial account with the collaboration (e.g. the shared fund to pay for medical expenses).

The process continues to block 704, where the system identifies a first future action of the one or more future actions and a total resource amount associated with addressing the first future action. The first future action may, for example, be a specific medical procedure required under the current treatment plan for the patient. The system may first determine whether the first determine whether the first future action falls within the scope of the types of actions designed to be funded by the collaboration, which may be based on availability of funds, purpose of the future action, insurance coverage, and the like. The system may then calculate the total resource amount (e.g. total amount of funds) necessary for covering the medical procedure. This may be accomplished by obtaining an invoice from a healthcare provider in the area. Alternatively, the total resource amount may be estimated using historical data from similarly situated patients.

In some embodiments, the system may use a dashboard in the resource viewing panel to show contributions to a medical care fund from various sources. For instance, the system may display to users information on the funds contributed by other caregivers, insurance payouts, third parties, and the like. The system may further track and display information relevant for tax and accounting purposes, such as miles spent transporting the patient. The system may generate reports of the aggregated account data to users to simplify the submission of tax or accounting records by the user.

The process continues to block 705, where the system transmits, to the computing device of the second user, a request to approve a transfer of a first amount of resources from the resource account of the second user to a combined resource account associated with addressing the first action. The combined resource account may be a financial account specifically created to pay for the medical expenses of the patient. The second user (e.g. a caregiver) may be asked to approve a transfer of funds from the second user's account to the combined resource account in the amount as determined in the above steps. The system may present the request as a notification on the second user's computing device, where the notification may contain information such as the exact amount of funds to be transferred, the purpose of the transfer, current account balance in the combined resource account, and the like. In some embodiments, the second user may, rather than a relative of the patient, be a third party who wishes to contribute to a patient's medical fund. In such an embodiment, the second user may have elected to contribute through a crowdfunding or social media platform.

The process continues to block 706, where the system transmits, to the computing device of the third user, a request to approve a transfer of a second amount of resources from the resource account of the third user to a combined resource account associated with addressing the first action. Again, the combined resource account may be a financial account specifically created to pay for the medical expenses of the patient. The third user (e.g. a caregiver) may be asked to approve a transfer of funds from the third user's account to the combined resource account in the amount as determined in the above steps. In some embodiments, the system may request funds for the combined resource account as bills for medical expenses become due. In other embodiments, the system may collect funds in the account prospectively based on future foreseeable expenses. In some embodiments, the system may extend a line of credit to a caregiver in the event that the caregiver is unable to contribute financially. For instance, the system may calculate a monetary value of a certain caregiver action and accept the action in lieu of a funding contribution. For instance, the patient may place a higher value on receiving transportation from a caregiver over a third party transportation service. In this way, the system accounts for non-financial contributions made by caregivers for the care of the patient.

Looking now to FIG. 7B, the process from FIG. 7A continues to block 707, where the system receives, from the computing device of the second user, an acceptance to transfer the first amount of resources from the resource account of the second user to the combined resource account. The second user may authorize transfer of designated funds through the second user's computing device. In some embodiments, the second user may provide the system with the credentials needed to authorize the bank transfer. In other embodiments, the second user may sign in separately to the financial institution associated with the second user's account to authorize the transfer.

The process continues to block 708, where the system transfers the first amount of resources from the resource account of the second user to the combined resource account. The system transfers the funds from the second user into the combined account for paying for the patient's medical expenses. The system may update a visual representation of the funds in the combined account and further contain information on the amounts of payments received from specific caregivers, and may report outstanding receivables.

The process continues to block 709, where the system receives, from the computing device of the third user, an acceptance to transfer the second amount of resources from the resource account of the third user to the combined resource account. The third user may authorize transfer of designated funds through the third user's computing device. In some embodiments, the third user may provide the system with the credentials needed to authorize the bank transfer. In other embodiments, the third user may sign in separately to the financial institution associated with the third user's account to authorize the transfer.

The process continues to block 710, where the system transfers the second amount of resources from the resource account of the third user to the combined resource account. In an exemplary embodiment, the second user and the third user have contributed all of the funds necessary for the future action (e.g. the first amount of resources and the second amount of resources). In such an embodiment, the system may determine that a sufficient amount of funds has been collected from each of the designated caregivers to fund the medical procedure. The system may then send a notification to said caregivers that the full amount of funds has been collected.

The process concludes at block 711, where the system transfers the total resource amount from the combined resource account to one or more merchants associated with the first future action. The one or more merchants may be the healthcare provider(s) that provide the medical treatment or procedure to the patient. The system may be configured to delay transferring the total resource amount until the insurance company of the patient has accepted a claim for the treatment.

Referring now to FIG. 8, a method for receiving transmissions from disparate nods and triggering automatic portal action(s) is illustrated. As discussed above, embodiments of the invention provide for a system that receives transmissions from disparate nodes and triggers automatic portion action. In some embodiments, the system provides for patient self-reporting of status information in order to leverage a caregiver portion action as described herein. In addition to receiving and aggregating data from financial sources, Internet of Things (IOT) sources, patient mobile devices and the like, the system also receive status updates manually from the patient. The system may rely on known information regarding the patient's schedule and timeline to pose questions or suggestions to the patient regarding possible updates. For example, if the time for an appointment has arrived, the portal may push a notification to the patient's mobile device requesting that the patient confirm that the patient has arrived for the appointment. This interaction also provides that patient an easy way to report difficulties or problems by predicting likely problems and requesting confirmation from the patient that they are experiencing the predicted type of problem. Appropriate notifications can then be sent to caregivers and/or additional automatic actions may be taken to mitigate the confirmed problem.

As shown in FIG. 8, the first step, as illustrated by block 800, is to provide a responder application to one or more users associated with a first user for installation on remote computing devices of the one or more users. The next step, as illustrated by block 801, is to monitor, continuously in some cases, a computing device associated with the first user for an indication of a status change for a status of the first user. The next step, as illustrated by block 802, is to identify, from the computing device associated with the first user, the indication of the status change for the first user. The indication of the status change was received from the first user via input to the computing device.

In various embodiments, the patient (or first user) may self-report status information in order to trigger some caregiver portal action as discussed here. The patient's mobile device may prompt the patient to input particular information. The mobile device may recognize that the patient is traveling and the mobile device may prompt the patient to confirm the patient's travel plans including destination, timing, etc. The mobile device may recognize from the patient's electronic calendar an appointment and may prompt the patient to confirm his or her travel plans once it recognizes the mobile device is moving. In another example, the patient may provide input when an appointment is coming to an end so that, for example, the patient's travel arrangements may be effectively implemented.

The next step, as represented by block 803, is, in response to identifying the indication of the status change for the first user, to identify a responsive action associated with the status change of the first user. The next step, as represented by block 804, is, in response to determining the responsive action, to transmit a responsive action alert over a wireless communication channel to a mobile computing device of a second user of the one or more users.

In various embodiments, the system provides a user settings option for using geo-location capabilities of the patient's mobile device to provide automatic status updates to the portal. For example, the patient or a caregiver may indicate a preference for geo-location to provide automated status updates to the portal and when the patient's mobile device is moving, updates may be pushed to the portal for appropriate notifications to be sent to the patient and/or caregivers. In some embodiments, the portal provides for monitoring the patient's location via geo-location and confirms that the patient is in a particular location only once the patient has been in that location for a predetermined period of time, such as fifteen (15) minutes or one (1) hour. Such time period may be related to an appointment on the patient's schedule, such as a doctor's appointment that is expected to last for thirty (30) minutes may dictate to the portal that the predetermined period of time for confirming the patient's location is ten (10) minutes or fifteen (15) minutes. In some cases, the portal may conclude the patient is in a particular location after a percentage of the total time of the appointment has passed, such as one third (⅓) or one half (½) of the appointment time.

In various embodiments of the portal, historical behaviors of the patient may be analyzed in predicting current or future behaviors. For example, if the patient is moving but is believed to be headed in a different direction than to the upcoming appointment, then the portal may review the patient's historical travel and predict that the patient is headed to a location previously visited for another appointment. More specifically, the patient may be confused regarding which doctor's appointment is that day and may be traveling to the wrong doctor's office. The system may recognize this and send the patient and/or caregiver's a notification of the mistake. The portal may also automatically inform the predicted location (if it is a known destination) of the patient's mistake and trigger one or more additional actions to assist the patient in resolving the mistake. One example would be to initiate a caregiver to intercept the patient on their current path or at the expected destination and assist the patient in traveling to the correct location for the appointment.

In some embodiments, the portal provides for automatic settling of matters after a given appointment. This may include financial settlement for debts owed because of an appointment on the user's calendar. One example of this may be a visit to a doctor's office. The portal may receive information from the doctor's office regarding the payment required for the visit once it has been completed (or during the visit) and make arrangements for payment (or cause payment to be made) based on settings associated with the user's accounts or portal profile preferences. In one extended example, a doctor may recommend particular testing, which may be recognized by voice recognition running on the patient's mobile device. In some cases, the patient may input the recommended treatment or other expenditure or may confirm the mobile device has accurately recognized the recommended treatment or expenditure. The device may communicate with the portal to determine, based, on the patient's portal profile including insurance and financial information, the out-of-pocket cost to the patient. The determined cost may be communicated immediately to the patient and/or the patient's caregiver network. In this regard, real-time treatment decisions may be made by the patient or caregiver based on accurate financial impact information. Once the treatment or visit has been completed, payment may be automatically completed or scheduled for future payment. In some instances, a set of business rules or criteria for evaluating a particular obligation or treatment in the above example may be implemented for assisting the patient in making educated financial decisions. For example, financial outlay thresholds may be set in the patient's portal profile that prohibit the patient from making decisions involving, for example, one hundred dollars ($100) of obligations without input from a designated caregiver. In some cases, the payment mechanism (checking, credit, caregiver account or otherwise) may be dictated by the payment amount or the type of obligation (medical visit, prescription, other pharmacy, grocery, etc.). For some types of obligations, the payment may be made immediately with the designated payment mechanism and for other types of obligations, the payment may be scheduled for a later date (and may require approval from a caregiver).

Each communication interface described herein generally includes hardware, and, in some instances, software, that enables the computer system, to transport, send, receive, and/or otherwise communicate information to and/or from the communication interface of one or more other systems on the network. For example, the communication interface of the user input system may include a wireless transceiver, modem, server, electrical connection, and/or other electronic device that operatively connects the user input system to another system. The wireless transceiver may include a radio circuit to enable wireless transmission and reception of information.

As will be appreciated by one of ordinary skill in the art, the present invention may be embodied as an apparatus (including, for example, a system, a machine, a device, a computer program product, and/or the like), as a method (including, for example, a business process, a computer-implemented process, and/or the like), or as any combination of the foregoing. Accordingly, embodiments of the present invention may take the form of an entirely software embodiment (including firmware, resident software, microcode, and the like), an entirely hardware embodiment, or an embodiment combining software and hardware aspects that may generally be referred to herein as a "system." Furthermore, embodiments of the present invention may take the form of a computer program product that includes a computer-readable storage medium having computer-executable program code portions stored therein.

As the phrase is used herein, a processor may be "configured to" perform a certain function in a variety of ways, including, for example, by having one or more general-purpose circuits perform the function by executing particular computer-executable program code embodied in computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, infrared, electromagnetic, and/or semiconductor system, apparatus, and/or device. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as a propagation signal including computer-executable program code portions embodied therein.

It will also be understood that one or more computer-executable program code portions for carrying out the specialized operations of the present invention may be required on the specialized computer include object-oriented, scripted, and/or unscripted programming languages, such as, for example, Java, Perl, Smalltalk, C++, SAS, SQL, Python, Objective C, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

It will also be understood that the one or more computer-executable program code portions may be stored in a transitory or non-transitory computer-readable medium (e.g., a memory, and the like) that can direct a computer and/or other programmable data processing apparatus to function in a particular manner, such that the computer-executable program code portions stored in the computer-readable medium produce an article of manufacture, including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with operator and/or human-implemented steps in order to carry out an embodiment of the present invention.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system for receiving transmissions from disparate nodes and triggering automatic portion action, the system comprising:
    a non-transitory computer-readable memory device with computer-readable program code stored thereon; and
    one or more processing devices operatively coupled to the memory device, wherein the one or more processing devices are configured to execute the computer-readable program code to:
        provide a responder application to one or more users associated with a first user for installation on remote computing devices of the one or more users;

monitor, continuously, a computing device associated with the first user, an indication of a status change for a status of the first user, wherein monitoring further comprises:
  initiate a communication signal to be transmitted to the computing device associated with the first user, wherein the communication signal is configured to cause the computing device to trigger an image capturing device and a microphone embedded in the computing device associated with the user; and
  receive electronic signals from the computing device associated with the first user, wherein the electronic signals comprises at least a video signal and an audio signal captured via the image capturing device and the microphone;
identify, from the computing device associated with the first user, the indication of the status change for the first user based on at least monitoring the computing device associated with the first user;
in response to identifying the indication of the status change for the first user, identify a responsive action associated with the status change of the first user;
in response to determining the responsive action, transmit a responsive action alert over a wireless communication channel to a mobile computing device of a second user of the one or more users, wherein the responsive action alert activates the responder application stored on the mobile computing device of the second user to cause the mobile computing device of the second user to display a notification of the status change for the first user and the responsive action associated with the status change of the first user in real time;
receive an indication that the user has implemented the responsive action associated with the status change of the first user;
determine one or more recommended future actions based on at least the status change, and the responsive action;
transmit control signals configured to cause the computing device of the first user to display the one or more recommended future actions to the first user to be implemented, wherein implementing the one or more recommended future actions reduces a likelihood of the status change of the user from occurring again; and
receive an indication that the user has implemented the one or more recommended future actions.

2. The system of claim 1, wherein the one or more processing devices are further configured to execute computer-readable program code to:
in response to identifying the responsive action associated with the status change of the first user, compare the responsive action with a database comprising accepted responsibilities associated with each of the one or more users associated with the first user to determine a match between the responsive action and the second user.

3. The system of claim 1, wherein the one or more processing devices are further configured to execute computer-readable program code to:
in response to identifying the indication of the status change for the first user, identify an additional responsive action associated with the status change of the first user; and
in response to determining the additional responsive action, transmit an additional responsive action alert over a wireless communication channel to a mobile computing device of a third user of the one or more users, wherein the additional responsive action alert activates the responder application stored on the mobile computing device of the third user to cause the mobile computing device of the third user to display the notification of the status change for the first user and the additional responsive action associated with the status change of the first user.

4. The system of claim 1, wherein the one or more processing devices are further configured to execute computer-readable program code to:
facilitate at least a portion of the responsive action.

5. The system of claim 4, wherein facilitating the at least the portion of the responsive action comprises initiating and processing a financial transaction associated with the responsive action.

6. The system of claim 4, wherein facilitating the at least the portion of the responsive action comprises displaying a current geographic location of the first user in real time on the mobile computing device of the second user.

7. The system of claim 1, wherein the computing device associated with the first user is configured to:
detect or measures a health indicator of the first user, a geographic location of the first user, or financial transactions of the first user for a triggering event associated with the status change; and
in response to detecting the triggering event, transmit the indication of the status change.

8. A computer program product for monitoring device data to cause remote mobile computing devices to alert users to take actions for updating a status of a different user, the computer program product comprising at least one non-transitory computer readable medium comprising computer readable instructions, the instructions comprising instructions for:
providing a responder application to one or more users associated with a first user for installation on remote computing devices of the one or more users;
monitoring, continuously, a computing device associated with the first user, an indication of a status change for a status of the first user, wherein monitoring further comprises:
  initiate a communication signal to be transmitted to the computing device associated with the first user, wherein the communication signal is configured to cause the computing device to trigger an image capturing device and a microphone embedded in the computing device associated with the user; and
  receive electronic signals from the computing device associated with the first user, wherein the electronic signals comprises at least a video signal and an audio signal captured via the image capturing device and the microphone;
identifying, from the computing device associated with the first user, the indication of the status change for the first user based on at least monitoring the computing device associated with the first user;
in response to identifying the indication of the status change for the first user, identifying a responsive action associated with the status change of the first user;
in response to determining the responsive action, transmitting a responsive action alert over a wireless communication channel to a mobile computing device of a second user of the one or more users, wherein the responsive action alert activates the responder application stored on the mobile computing device of the second user to cause the mobile computing device of the second user to display a notification of the status change for the first user and the responsive action associated with the status change of the first user in real time;

receiving an indication that the user has implemented the responsive action associated with the status change of the first user;

determining one or more recommended future actions based on at least the status change, and the responsive action;

transmitting control signals configured to cause the computing device of the first user to display the one or more recommended future actions to the first user to be implemented, wherein implementing the one or more recommended future actions reduces a likelihood of the status change of the user from occurring again; and receiving an indication that the user has implemented the one or more recommended future actions.

9. The computer program product of claim 8, wherein the computer readable instructions further comprise instructions for:

in response to identifying the responsive action associated with the status change of the first user, comparing the responsive action with a database comprising accepted responsibilities associated with each of the one or more users associated with the first user to determine a match between the responsive action and the second user.

10. The computer program product of claim 8, wherein the computer readable instructions further comprise instructions for:

in response to identifying the indication of the status change for the first user, identifying an additional responsive action associated with the status change of the first user; and in response to determining the additional responsive action, transmitting an additional responsive action alert over a wireless communication channel to a mobile computing device of a third user of the one or more users, wherein the additional responsive action alert activates the responder application stored on the mobile computing device of the third user to cause the mobile computing device of the third user to display the notification of the status change for the first user and the additional responsive action associated with the status change of the first user.

11. The computer program product of claim 8, wherein the computer readable instructions further comprise instructions for:

facilitating at least a portion of the responsive action.

12. The computer program product of claim 11, wherein facilitating the at least the portion of the responsive action comprises initiating and processing a financial transaction associated with the responsive action.

13. The computer program product of claim 11, wherein facilitating the at least the portion of the responsive action comprises displaying a current geographic location of the first user in real time on the mobile computing device of the second user.

14. The computer program product of claim 8, wherein the computer readable instructions further comprise instructions for:

detecting or measures a health indicator of the first user, a geographic location of the first user, or financial transactions of the first user for a triggering event associated with the status change; and in response to detecting the triggering event, transmitting the indication of the status change.

15. A computer implemented method for monitoring device data to cause remote mobile computing devices to alert users to take actions for updating a status of a different user, said computer implemented method comprising:

providing a computing system comprising a computer processing device and a non-transitory computer readable medium, where the computer readable medium comprises configured computer program instruction code, such that when said instruction code is operated by said computer processing device, said computer processing device performs the following operations:

providing a responder application to one or more users associated with a first user for installation on remote computing devices of the one or more users;

monitoring, continuously, a computing device associated with the first user, an indication of a status change for a status of the first user, wherein monitoring further comprises:

initiate a communication signal to be transmitted to the computing device associated with the first user, wherein the communication signal is configured to cause the computing device to trigger an image capturing device and a microphone embedded in the computing device associated with the user; and receive electronic signals from the computing device associated with the first user, wherein the electronic signals comprises at least a video signal and an audio signal captured via the image capturing device and the microphone;

identifying, from the computing device associated with the first user, the indication of the status change for the first user based on at least monitoring the computing device associated with the first user;

in response to identifying the indication of the status change for the first user, identifying a responsive action associated with the status change of the first user;

in response to determining the responsive action, transmitting a responsive action alert over a wireless communication channel to a mobile computing device of a second user of the one or more users, wherein the responsive action alert activates the responder application stored on the mobile computing device of the second user to cause the mobile computing device of the second user to display a notification of the status change for the first user and the responsive action associated with the status change of the first user in real time;

receiving an indication that the user has implemented the responsive action associated with the status change of the first user;

determining one or more recommended future actions based on at least the status change, and the responsive action;

transmitting control signals configured to cause the computing device of the first user to display the one or more recommended future actions to the first user to be implemented, wherein implementing the one or more recommended future actions reduces a likelihood of the status change of the user from occurring again; and receiving an indication that the user has implemented the one or more recommended future actions.

16. The computer implemented method of claim 15, further comprising:

in response to identifying the responsive action associated with the status change of the first user, comparing the responsive action with a database comprising accepted responsibilities associated with each of the one or more users associated with the first user to determine a match between the responsive action and the second user.

17. The computer implemented method of claim 15, further comprising:

in response to identifying the indication of the status change for the first user, identifying an additional responsive action associated with the status change of the first user; and in response to determining the additional responsive action, transmitting an additional responsive action alert over a wireless communication channel to a mobile computing device of a third user of the one or more users, wherein the additional responsive action alert activates the responder application stored on the mobile computing device of the third user to cause the mobile computing device of the third user to display the notification of the status change for the first user and the additional responsive action associated with the status change of the first user.

18. The computer implemented method of claim 15, further comprising:

facilitating at least a portion of the responsive action.

19. The computer implemented method of claim 18, wherein facilitating the at least the portion of the responsive action comprises (i) initiating and processing a financial transaction associated with the responsive action or (ii) displaying a current geographic location of the first user in real time on the mobile computing device of the second user.

20. The computer implemented method of claim 15, further comprising:

detecting or measures a health indicator of the first user, a geographic location of the first user, or financial transactions of the first user for a triggering event associated with the status change; and in response to detecting the triggering event, transmitting the indication of the status change.

\* \* \* \* \*